US006274583B1

(12) United States Patent
Patane et al.

(10) Patent No.: US 6,274,583 B1
(45) Date of Patent: Aug. 14, 2001

(54) ALPHA 1A ADRENERGIC RECEPTOR ANTAGONISTS

(75) Inventors: Michael A. Patane, Harleysville; Mark G. Bock, Hatfield; Randall C. Newton, West Point, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/345,652

(22) Filed: Jun. 30, 1999

Related U.S. Application Data

(60) Division of application No. 08/973,624, filed as application No. PCT/US96/09425 on Jun. 6, 1996, now Pat. No. 5,977,115, which is a continuation-in-part of application No. 08/488,272, filed on Jun. 7, 1995, now Pat. No. 5,661,163.

(51) Int. Cl.$^7$ ....................... A61K 31/495; C07D 295/12
(52) U.S. Cl. ................. 514/255; 544/380; 544/381; 544/393; 544/396; 544/400
(58) Field of Search ............... 514/255; 544/380, 544/381, 393, 396, 400

(56) References Cited

U.S. PATENT DOCUMENTS

| | | | |
|---|---|---|---|
| 2,722,529 | * 11/1955 | Fleming et al. | 544/393 |
| 2,833,770 | 5/1958 | Parcell | 260/268 |
| 3,340,143 | 9/1967 | Bernstein | 167/53.1 |
| 4,031,226 | 6/1977 | Soudijn et al. | 424/267 |
| 4,069,221 | 1/1978 | Yonan | 260/293.62 |
| 4,369,184 | 1/1983 | Stokbroekx et al. | 424/267 |
| 4,699,910 | 10/1987 | Banholzer | 514/255 |
| 5,403,847 | 4/1995 | Gluchowski et al. | 514/318 |
| 5,620,993 | 4/1997 | Patane et al. | 514/321 |
| 5,661,163 | 8/1997 | Patane et al. | 514/331 |

FOREIGN PATENT DOCUMENTS

| | | |
|---|---|---|
| 0 048 045 | 3/1982 | (EP) . |
| 0 374 095 | 6/1990 | (EP) . |
| 2004986 | 6/1990 | (EP) . |
| 0 442 242 A1 | 8/1991 | (EP) . |
| 0 496 692 A1 | 7/1992 | (EP) . |
| 0 757 986 A1 | 2/1997 | (EP) . |
| 1 166 364 | 10/1969 | (GB) . |
| 1 206 487 | 9/1970 | (GB) . |
| 2 014 145 | 8/1979 | (GB) . |
| WO 94/08040 | 4/1994 | (WO) . |
| WO 94/10989 | 5/1994 | (WO) . |
| WO 94/21660 | 9/1994 | (WO) . |
| WO 94/22829 | 10/1994 | (WO) . |
| WO 94/26735 | 11/1994 | (WO) . |
| WO 95/04049 | 2/1995 | (WO) . |
| WO 95/07075 | 3/1995 | (WO) . |
| WO 96/14846 | 5/1996 | (WO) . |
| WO 97/37983 | 10/1997 | (WO) . |

OTHER PUBLICATIONS

Agarwal et al. "Substituted piperazinoureas as . . . " CA 74:112001, 1971.*
J. M. Wetzel et al., "Discovery of Alpha 1a Adrenergic Receptor Antagonists . . . ", J. of Med. Chem., vol. 38, No. 10, pp. 1579–1581 (1995).
I. Roufos et al., "A structure—Activity Relationship Study of Novel Phenylacetamides . . . ", J. Med. Chem., vol. 39, No. 7, pp. 1514–1520 (1996).
M. El–Bernawy, "4–[Noradamantanecarboxamido)Butyl] –1–(2–Methoxyphenyl) . . . ", Med. Chem. Res., vol. 2, No. 2, pp. 88–94 (1992).

* cited by examiner

Primary Examiner—Ceila Chang
(74) Attorney, Agent, or Firm—Catherine D. Fitch; Kenneth R. Walton; Melvin Winokur

(57) ABSTRACT

This invention relates to certain novel compounds and derivatives thereof, their synthesis, and their use as selective alpha-1a adrenergic receptor antagonists. One application of these compounds is in the treatment of benign prostatic hyperplasia. These compounds are selective in their ability to relax smooth muscle tissue enriched in the alpha 1a receptor subtype without at the same time inducing orthostatic hypotension. One such tissue is found surrounding the urethral lining. Therefore, one utility of the instant compounds is to provide acute relief to males suffering from benign prostatic hyperplasia, by permitting less hindered urine flow. Another utility of the instant compounds is provided by combination with a human 5-alpha reductase inhibitory compound, such that both acute and chronic relief from the effects of benign prostatic hyperplasia are achieved.

25 Claims, No Drawings

ALPHA 1A ADRENERGIC RECEPTOR ANTAGONISTS

This application is a division of U.S. Ser. No. 08/973,624, filed Dec. 4, 1997, now U.S. Pat. No. 5,977,115, which is the national stage of PCT/US96/09425, filed Jun. 6, 1996, which is a continuation-in-part of U.S. Ser. No. 08/488,272, filed Jun. 7, 1995, now U.S. Pat. No. 5,661,163, the contents of which are hereby incorporated by reference.

FIELD OF THE INVENTION

This invention relates to certain novel compounds and derivatives thereof, their synthesis, and their use as selective alpha-1a adrenoceptor antagonists. More particularly, the compounds of the present invention are useful for treating benign prostatic hyperplasia (BPH).

BACKGROUND OF THE INVENTION

Human adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: alpha receptors bind norepinephrine more strongly than epinephrine and much more strongly than the synthetic compound isoproterenol. The binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into $\alpha_1$, $\alpha_2$, $\beta_1$, and $\beta_2$ subtypes. Functional differences between $\alpha_1$ and $\alpha_2$ receptors have been recognized, and compounds which exhibit selective binding between these two subtypes have been developed. Thus, in WO 92/0073, the selective ability of the R(+) enantiomer of terazosin to selectively bind to adrenergic receptors of the alpha 1 subtype was reported. The $\alpha_1/\alpha_2$ selectivity of this compound was disclosed as being significant because agonist stimulation of the $\alpha_2$ receptors was said to inhibit secretion of epinephrine and norepinephrine, while antagonism of the $\alpha_2$ receptor was said to increase secretion of these hormones. Thus, the use of non-selective alpha-adrenergic blockers, such as phenoxybenzamine and phentolamine, is limited by their $\alpha_2$ adrenergic receptor mediated induction of increased plasma catecholamine concentration and the attendant physiological sequelae (increased heart rate and smooth muscle contraction).

For a general background on the $\alpha$-adrenergic receptors, the reader's attention is directed to Robert R. Ruffolo, Jr., $\alpha$-Adrenoreceptors: Molecular Biology, Biochemistry and Pharmacology, (Progress in Basic and Clinical Pharmacology series, Karger, 1991), wherein the basis of $\alpha_1/\alpha_2$ subclassification, the molecular biology, signal transduction (G-protein interaction and location of the significant site for this and ligand binding activity away from the 3'-terminus of alpha adrenergic receptors), agonist structure-activity relationships, receptor functions, and therapeutic applications for compounds exhibiting $\alpha$-adrenergic receptor affinity was explored.

The cloning, sequencing and expression of alpha receptor subtypes from animal tissues has led to the subclassification of the $\alpha_1$ receptors into $\alpha_{1a}$, (Lomasney, et al., J. Biol. Chem., 266:6365–6369 (1991), rat $\alpha_{1a}$; Bruno et al., BBRC, 179:1485–1490 (1991), human $\alpha_{1a}$), ($\alpha_{1b}$ (Cotecchia, et al., PNAS, 85;7159–7163 (1988), hamster $\alpha 1_b$; Libert, et al., Science, (1989), dog $\alpha_{1b}$; Ramarao, et al., J. Biol. Chem., 267:21936–21945 (1992), human $\alpha_{1b}$, and most recently, in a study using bovine brain, a new $\alpha_{1c}$ subtype was proposed (Schwinn, et al., J. Biol. Chem., 265:8183–8189 (1990); Hirasawa et al., BBRC 195:902–909 (1993), described the cloning, functional expression and tissue distribution of a human $\alpha_{1c}$ adrenergic receptor; Hoehe et al., Human Mol. Genetics 1 (5):349 (8/92) noted the existence of a two-allele Pst1 restriction fragment polymorphism in the $\alpha_{1c}$ adrenergic receptor gene; another study suggests that there may even be an alpha-1d receptor subtype, see Perez et al., Mol. Pharm., 40:876–883, 1992). Each $\alpha_1$ receptor subtype exhibits its own pharmacologic and tissue specificities. Schwinn and coworkers noted that the cloned bovine $\alpha_{1c}$ receptor exhibited pharmacological properties proposed for the $\alpha_{1a}$ subtype. Nonetheless, based on its non-expression in tissues where the $\alpha_{1a}$ subtype is expressed, and its sensitivity to chloroethylclonidine, the receptor was given a new designation.

The differences in the $\alpha$-adrenergic receptor subtypes have relevance in pathophysiologic conditions. Benign prostatic hyperplasia, also known as benign prostatic hypertrophy or BPH, is an illness typically affecting men over fifty years of age, increasing in severity with increasing age. The symptoms of the condition include, but are not limited to, increased difficulty in urination and sexual dysfunction. These symptoms are induced by enlargement, or hyperplasia, of the prostate gland. As the prostate increases in size, it impinges on free-flow of fluids through the male urethra. Concomitantly, the increased noradrenergic innervation of the enlarged prostate leads to an increased adrenergic tone of the bladder neck and urethra, further restricting the flow of urine through the urethra.

In benign prostatic hyperplasia, the male hormone 5α-dihydrotestosterone has been identified as the principal culprit. The continual production of 5α-dihydrotestosterone by the male testes induces incremental growth of the prostate gland throughout the life of the male. Beyond the age of about fifty years, in many men, this enlarged gland begins to obstruct the urethra with the pathologic symptoms noted above.

The elucidation of the mechanism summarized above has resulted in the recent development of effective agents to control, and in many cases reverse, the pernicious advance of BPH. In the forefront of these agents is Merck & Co., Inc.s' product PROSCAR® (finasteride).

The effect of this compound is to inhibit the enzyme testosterone 5-alpha reductase, which converts testosterone into 5α-dihydrotesterone, resulting in a reduced rate of prostatic enlargement, and often reduction in prostatic mass.

The development of such agents as PROSCAR® bodes well for the long-term control of BPH. However, as may be appreciated from the lengthy development of the syndrome, its reversal also is not immediate. In the interim, those males suffering with BPH continue to suffer, and may in fact lose hope that the agents are working sufficiently rapidly.

In response to this problem, one solution is to identify pharmaceutically active compounds which complement slower-acting therapeutics by providing acute relief. Agents which induce relaxation of the urethral smooth muscle, by binding to alpha-1 adrenergic receptors, thus reducing the increased adrenergic tone due to the disease, would be good candidates for this activity. Thus, one such agent is alfuzosin, which is reported in EP 0 204597 to induce urination in cases of prostatic hyperplasia. Likewise, in WO 92/0073, the selective ability of the R(+) enantiomer of terazosin to bind to adrenergic receptors of the $\alpha_1$ subtype was reported. In addition, in WO 92/161213, hereby incorporated by reference, combinations of 5-alpha-reductase inhibitory compounds and alpha1-adrenergic receptor blockers (terazosin, doxazosin, prazosin, bunazosin, indoramin, alfuzosin) were disclosed. However, no information as to the $\alpha_{1a}$, $\alpha_{1b}$, or $\alpha_{1c}$ subtype specificity of these compounds was provided as this data and its relevancy to the treatment of BPH was not known. Current therapy for BPH uses existing non-selective alpha-1 antagonists such as prazosin (Minipress, Pfizer), Terazosin (Hytrin, Abbott) or doxazosin mesylate (Cardura, Pfizer). These non-selective antagonists suffer from side effects related to antagonism of the alpha-1a and alpha-1b receptors in the peripheral vasculature, e.g., orthostatic hypotension and syncope.

Typically, identification of active compounds is accomplished through use of animal tissues known to be enriched in adrenergic receptors. Thus, rat tissues have been used to screen for potential adrenergic receptor antagonists. However, because of species variability, compounds which appear active in animal tissue may not be active or sufficiently selective in humans. This results in substantial wastage of time and effort, particularly where high volume compound screening programs are employed. There is also the danger that compounds, which might be highly effective in humans, would be missed because of their absence of appreciable affinity for the heterologous animal receptors. In this regard, it has been noted that even single amino acid changes between the sequence of biologically active proteins in one species may give rise to substantial pharmacological differences. Thus, Fong et al., (*J. Biol. Chem.,* 267:25668–25671, 1992) showed that there are 22 divergent amino acid residues between the sequence of the human neurokinin-1 receptor and the homologous rat receptor. They further showed, in studies with mutant receptors, that substitution of only two amino acid residues was both necessary and sufficient to reproduce the rat receptor's antagonist binding affinity in the human receptor. Oksenberg et al., (*Nature,* 360:161–163, 1992) showed that a single amino-acid difference confers major pharmacological variation between the human and the rodent 5-hydroxytryptamine receptors. Likewise, Kuhse et al., (*Neuron,* 5:867–873, 1990) showed that a single amino-acid exchange alters the pharmacology of the neonatal rat glycine receptor subunit. This difficulty and unpredictability has resulted in a need for a compound screen which will identify compounds that will be active in humans.

These problems were solved by cloning the human adrenergic receptor of the $\alpha_{1c}$ subtype (ATCC CRL 11140) and the use of a screening assay which enables identification of compounds which specifically interact with the human α1c adrenergic receptor. [PCT International Application Publication Nos. WO94/08040, published Apr. 14, 1994 and WO94/10989, published May 26, 1994] As disclosed in the instant patent disclosure, a cloned human $\alpha_{1c}$ adrenergic receptor and a method for identifying compounds which bind the human $\alpha_{1c}$ receptor has now made possible the identification of selective human $\alpha_{1c}$ adrenergic receptor antagonists useful for treating BPH. The instant patent disclosure discloses novel compounds which selectively bind to the human $\alpha_{1c}$ receptor. These compounds are further tested for binding to other human alpha 1 receptor subtypes, as well as counterscreened against other types of receptors, thus defining the specificity of the compounds of the present invention for the human $\alpha_{1c}$ adrenergic receptor.

Compounds of this invention are used to reduce the acute symptoms of BPH. Thus, compounds of this invention may be used alone or in conjunction with a more long-term anti-BPH therapeutics, such as testosterone 5-alpha reductase inhibitors, including PROSCAR® (finasteride). Aside from their utility as anti-BPH agents, these compounds may be used to induce highly tissue-specific, localized $\alpha_{1c}$ adrenergic receptor blockade whenever this is desired. Effects of this blockade include reduction of intra-ocular pressure, control of cardiac arrhythmias, and possibly a host of alpha-1c receptor mediated central nervous system events.

Nomenclature

Recently, a new $\alpha_1$ adrenergic receptor ($\alpha_1$-AR) classification scheme similar to that proposed by Ford, et al. [$\alpha_1$-*Adrenoceptor Classification: Sharpening Occam's Razor, Trends in Pharm. Sci.* 1994, 15, 167–170] was adopted at the August, 1994 meeting of the International Union of Pharmacology (IUPHAR) in Montreal, Canada. The $\alpha_1$-AR genes formerly known as $\alpha_{1d}$, $\alpha_{1b}$ and $\alpha_{1c}$ were renamed $\alpha_{1d}$, $\alpha_{1b}$, and $\alpha_{1a}$, respectively. This new naming system reflects the correspondence between the proteins encoded by the $\alpha_{1a}$ and $\alpha_{1b}$ genes (new IUPHAR nomenclature) and the receptors characterized by traditional pharmacological means as $\alpha_{1A}$ and $\alpha_{1B}$, respectively, in the literature. Recombinant receptors and receptors characterized pharmacologically in tissues are distinguished by lowercase and uppercase subscripts, respectively.

The above discussion contained in the Background section used the former classification scheme (i.e., $\alpha_{1a/d}$, $\alpha_{1b}$ and $\alpha_{1c}$); however, hereinafter, the new classification scheme will be utilized (i.e., ($\alpha_{1d}$, $\alpha_{1b}$, and $\alpha_{1a}$). Thus, what was formerly referred to as the $\alpha_{1c}$ receptor (and $\alpha_{1c}$ receptor antagonists) will hereinafter be referred to utilizing the new nomenclature as the $\alpha_{1a}$ receptor (and $\alpha_{1a}$ receptor antagonists).

SUMMARY OF THE INVENTION

The present invention provides compounds for the treatment of urinary obstruction caused by benign prostatic hyperplasia (BPH). The compounds selectively antagonize the human alpha-1a adrenergic receptor at nanomolar and subnanomolar concentrations while exhibiting at least ten fold lower affinity for the alpha-1d and alpha-1b human adrenergic receptors and many other G-protein coupled receptors. This invention has the advantage over non-selective alpha-1 adrenoceptor antagonists of reduced side effects related to peripheral adrenergic blockade. Such side effects include orthostatic hypotension, syncope, lethargy, etc. The compounds of the present invention have the structure:

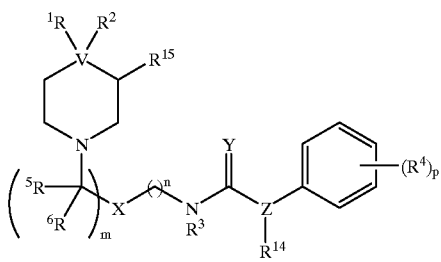

wherein

V is selected from carbon or nitrogen, provided that when V is nitrogen, then $R^2$ is absent;

X is selected from $CH_2$, $CHOR^5$, $CHF$, $CHR^5$, $CR^5R^6$, $CF_2$, $CHCHF_2$, $C=CF_2$ or $C=O$;

Y is selected from oxygen, $NR^8$ or sulfur;

Z is selected from CH, $CCO_2R^5$, $CH(CH_2)qCO_2(R^5)_2$, $COR^{12}$, $CNR^{12}R^{13}$ or $C(CH_2)qCN(R^5)_2$; or $Z-R^{14}$ forms a cyclopropyl ring;

$R^1$ is selected from unsubstituted, mono- or poly-substituted phenyl where the substitutents on the phenyl are independently selected from halogen, cyano, $CO_2R^5$, $OR^5$, $(CH_2)qCON(R^5)_2$, $(CH_2)qCO_2R^5$, methylenedioxy when the phenyl ring is di-substituted and the substituents are on adjacent carbon atoms, $C_{1-4}$ alkyl or halogen substituted $C_{1-4}$ alkyl; or unsubstituted, mono- or poly-substituted: pyridyl, thienyl, furanyl or naphthyl where the substituents on the pyridyl, thienyl, furanyl or naphthyl are independently selected from $CF_3$, phenyl, $OR^5$, halogen, $C_{1-4}$ alkyl or $C_{3-8}$ cycloalkyl;

$R^2$ is selected from hydrogen, cyano, $CO_2R^5$, $CON(R^5)_2$, tetrazole or isooxadiazole;

$R^3$ is selected from hydrogen, cyano, $CO_2R^5$, $CON(R^5)_2$, $C_{1-8}$ alkyl, $C_{3-8}$ cycloalkyl or $(CH_2)qCO_2R^5$;

$R^4$ is selected from hydrogen, $OR^5$, $C_{1-8}$ alkyl, halogen substituted $C_{1-4}$ alkyl, halogen or methylenedioxy when there are two $R^4$ substituents present on adjacent carbon atoms:

$R^5$ and $R^6$ are each independently selected from hydrogen, $C_{1-8}$ alkyl, $C_{3-8}$ cycloalkyl, halogen substituted $C_{1-4}$ alkyl and halogen substituted $C_{3-8}$ cycloalkyl;

$R^8$ is selected from hydrogen, cyano or $SO_2R^5$;

$R^{12}$ and $R^{13}$ are each independently selected from hydrogen, $C_{1-8}$ alkyl, $C_{3-9}$ cycloalkyl, CHO, $COR^5$, $CONR^5R^6$, $(CH_2)qOR^5$, $R^{14}$ is selected from hydrogen, $C_{1-8}$ alkyl, $C_{3-8}$ cycloalkyl, $C_{1-4}$ alkoxy, $N(R^5)_2$, morpholinyl, piperazinyl, d-valerolactamyl, 2-pyrrolidonyl, thienyl, furanyl, pyridinyl, naphthyl or unsubstituted, mono- or poly-substituted phenyl where the substituents on the phenyl are independently selected from $C_{1-4}$ alkyl, $N(R^5)_2$, $OR^5$ or halogen;

$R^{15}$ is selected from hydrogen or hydroxy;

m, n and q are each independently an integer of from zero to three, provided that when m and n are both zero, then X is selected from $CH_2$, CHF, $CHR^5$, $CR^5R^6$, $CF_2$, $CHCHF_2$, $C=CF_2$ or $C=O$; and p is an integer of from zero to five;

and the pharmaceutically acceptable salts thereof.

Preferably, $R^1$ is selected from unsubstituted, mono- or poly-substituted phenyl where the substitutents on the phenyl are independently selected from halogen, cyano, $CO_2R^5$, $OR^5$, $CON(R^5)_2$, methylenedioxy, $C_{1-4}$ alkyl or halogen substituted $C_{1-4}$ alkyl; pyridyl; thienyl; furanyl; or unsubstituted, mono- or poly-substituted naphthyl where the substituents on the naphthyl are independently selected from $CF_3$, phenyl, $OR^5$, halogen, $C_{1-4}$ alkyl or $C_{3-8}$ cycloalkyl; and p is an integer from 0 to 3.

In one embodiment of the invention is the compound wherein

Z is selected from CH, $CCO_2R^5$, $CH(CH_2)qCO_2(R^5)_2$, $COR^{12}$, $CNR^{12}R^{13}$ or $C(CH_2)qCN(R^5)_2$;

$R^1$ is selected from unsubstituted, mono- or poly-substituted phenyl where the substitutents on the phenyl are independently selected from halogen, cyano, $CO_2R^5$, $OR^5$, $(CH_2)qCON(R^5)_2$, $(CH_2)qCO_2R^5$ or $C_{1-4}$ alkyl; or unsubstituted, mono- or poly-substituted: pyridyl, thienyl, furanyl or naphthyl where the substituents on the pyridyl, thienyl, furanyl or naphthyl are independently selected from $CF_3$, phenyl, $OR^5$, halogen, $C_{1-4}$ alkyl or $C_{3-8}$ cycloalkyl;

$R^4$ is selected from hydrogen, $OR^5$, $C^{1-8}$ alkyl or halogen;

$R^{14}$ is selected from hydrogen, $C_{1-8}$ alkyl, $C_{3-8}$ cycloalkyl, $C_{1-4}$ alkoxy, morpholinyl, piperazinyl, δ-valerolactamyl, 2-pyrrolidonyl, thienyl, furanyl, pyridinyl, naphthyl or unsubstituted, mono- or poly-substituted phenyl where the substituents on the phenyl are independently selected from $C_{1-4}$ alkyl, $OR^5$ or halogen; and R15 is hydrogen; and all other variables are as defined above;

provided that when m and n are both zero, then X is selected from $CH_2$, CHF, $CHR^5$, $CR^5R^6$, $CF_2$, $CHCHF_2$, $C=CF_2$ or $C=O$;

and the pharmaceutically acceptable salts thereof.

In a class of the invention are the compounds of the formula

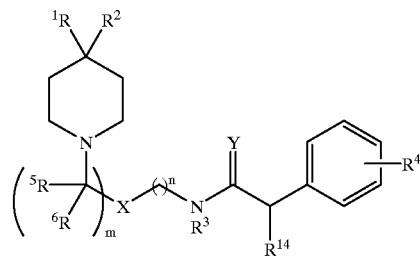

wherein $R^1$ is selected from unsubstituted, mono- or poly-substituted phenyl where the substitutents on the phenyl are independently selected from halogen, cyano, $CO_2R^5$, $OR^5$, $CON(R^5)_2$ or $C_{1-4}$ alkyl; pyridyl; thienyl; furanyl; or unsubstituted, mono- or poly-substituted naphthyl where the substituent on the naphthyl are independently selected from $CF_3$, phenyl, $OR^5$, halogen, $C_{1-4}$ alkyl or $C_{3-8}$ cycloalkyl; and all other variables are as defined above;

and the pharmaceutically acceptable salts thereof.

In a subclass of the invention is the compound of the formula

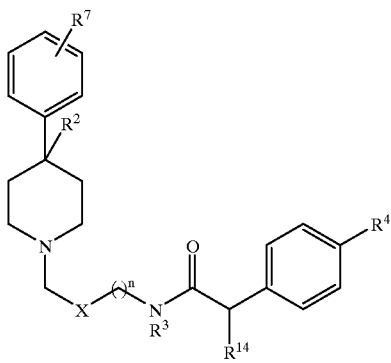

wherein
$R^2$ is selected from cyano or $CO_2R^5$;
$R^4$ is selected from hydrogen, halogen or $C_{1-4}$ alkyl;
$R^7$ is selected from hydrogen, $CF_3$, cyano, halogen or $C_{1-4}$ alkyl;
$R^{14}$ is selected from hydrogen, $C_{1-8}$ alkyl, $C_{3-8}$ cycloalkyl or unsubstituted, mono- or poly-substituted phenyl where the substitutent on the phenyl are independently selected from halogen or $C_{1-4}$ alkyl;
and where all other variables are as defined above;
and the pharmaceutically acceptable salts thereof.

Illustrative of the invention are the compounds of the formula

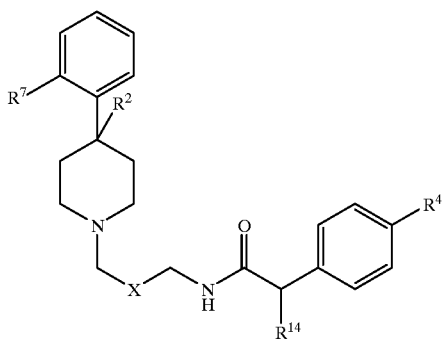

wherein
$R^5$ is $C_{1-4}$ alkyl;
$R^{14}$ is selected from $C_{3-8}$ cycloalkyl or unsubstituted or mono-substituted phenyl wherein the substituent is selected from halogen or $C_{1-4}$ alkyl; and where all other variables are as defined above;
and the pharmaceutically acceptable salts thereof.

Exemplifying the invention are the compounds wherein
X is selected from $CH_2$, CHOH or C=O;
$R^2$ is selected from cyano or $CO_2CH_3$;
$R^4$ is selected from hydrogen, chloro or methyl;
$R^7$ is selected from hydrogen, chloro or methyl; and
$R^{14}$ is selected from cyclopentyl, cyclohexyl, phenyl, p-tolyl or p-chlorophenyl;
and the pharmaceutically acceptable salts thereof.

Illustrating the invention is the compound selected from
2,2-Bis(4-chlorophenyl)-N-[3-(4-cyano-4-phenylpiperidin-1-yl)propylacetamide;
2,2-Bis(4-chlorophenyl)-N-[3-(4-cyano-4-{2-methylphenyl}piperidin-1-yl)propyl]acetamide;
2,2-Bis(4-chlorophenyl)-N-[3-(4-{2-chlorophenyl}4-cyanopiperidin-1-yl)propylacetamide;
2,2-Bis(4-methylphenyl)-N-[3-(4-cyano-4-phenylpiperidin-1-yl)propyl]acetamide hydrochloride;
2,2-Bis(4-methylphenyl)-N-[3-({4-carboxymethyl}4-phenylpiperidin-1-yl)propyl]acetamide hydrochloride;
2,2-Bis(4-methylphenyl)-N-[3-(4-cyano-4-{2-methylphenyl}piperidin-1-yl)propyl]acetamide;
2,2-Bis(4-methylphenyl)-N-[3-(4-{2-chlorophenyl}4-cyanopiperidine-1-yl)propyl]acetamide;
2,2-Bis(4-methylphenyl)-N-[3-(4-cyano-4-phenylpiperidin-1-yl)2-hydroxypropyl]acetamide;
2,2-Bis(4-methylphenyl)-N-[3-(4-cyano-4-{2-methylphenyl}piperidin-1-yl)2-hydroxypropyl]acetamide;
2,2-Bis(4-methylphenyl)-N-[3-(4-cyano-4-phenylpiperidine-1-yl)2-oxopropyl]acetamide;
2,2-Bis(4-methylphenyl)-N-[3-(4-cyano-4-{2-methylphenyl}piperidin-1-yl)2-oxopropyl]acetamide; or
2,2-Bis(4-methylphenyl)-N-[3-{4-(2-benzamido)piperizin-1-yl}-propyl]acetamide;
and the pharmaceutically acceptable salts thereof.

An illustration of the invention is a pharmaceutical composition comprising a therapeutically effective amount of any of the compounds described above and a pharmaceutically acceptable carrier. An example of the invention is a pharmaceutical composition made by combining any of the compounds described above and a pharmaceutically acceptable carrier. Another illustration of the invention is a process for making a pharmaceutical composition comprising combining any of the compounds described above and a pharmaceutically acceptable carrier.

Another example of the invention is the composition further comprising a therapeutically effective amount of a testosterone 5-alpha reductase inhibitor. Preferably, the testosterone 5-alpha reductase inhibitor is a type 1, a type 2, both a type 1 and a type 2 (i.e., a three component combination comprising any of the compounds described above combined with both a type 1 testosterone 5-alpha reductase inhibitor and a type 2 testosterone 5-alpha reductase inhibitor) or a dual type 1 and type 2 testosterone 5-alpha reductase inhibitor. More preferably, the testosterone 5-alpha reductase inhibitor is a type 2 testosterone 5-alpha reductase inhibitor. Most preferably, the testosterone 5-alpha reductase inhibitor is finasteride.

More specifically illustrating the invention is a method of treating benign prostatic hyperplasia in a subject in need thereof which comprises administering to the subject a therapeutically effective amount of any of the compounds (or any of the compositions) described above.

Further exemplifying the invention is the method of treating BPH wherein the compound (or composition) additionally does not cause a fall in blood pressure at dosages effective to alleviate BPH.

Another illustration of the invention is the method of treating benign prostatic hyperplasia wherein the compound is administered in combination with a testosterone 5-alpha reductase inhibitor. Preferably, the testosterone 5-alpha reductase inhibitor is finasteride.

Further illustrating the invention is a method of inhibiting contraction of prostate tissue or relaxing urethral smooth muscle in a subject in need thereof which comprises administering to the subject a therapeutically effective amount of any of the compounds (or any of the compositions) described above.

More specifically exemplifying the invention is the method of inhibiting contraction of prostate tissue or relaxing urethral smooth muscle wherein the compound (or composition) additionally does not cause a fall in blood pressures at dosages effective to inhibit contraction of prostate tissue.

More particularly illustrating the invention is the method of inhibiting contraction of prostate tissue or relaxing urethral smooth muscle wherein the compound (or composition) is administered in combination with a testosterone 5-alpha reductase inhibitor; preferably, the testosterone 5-alpha reductase inhibitor is finasteride.

More particularly exemplifying the invention is a method of treating a disease which is susceptible to treatment by antagonism of the alpha 1a receptor which comprises administering to a subject in need thereof an amount of any of the compounds described above effective to treat the disease. Diseases which are susceptible to treatment by antagonism of the alpha 1a receptor include, but are not limited to, BPH, high intraocular pressure, high cholesterol, impotency, sympathetically mediated pain and cardiac arrhythmia.

An additional illustration of the invention is the use of any of the compounds described above in the preparation of a medicament for: a) the treatment of benign prostatic hyperplasia; b) relaxing urethral smooth muscle; or c) inhibiting contraction of prostate tissue; in a subject in need thereof.

An additional example of the invention is a drug which is useful for: a) treating benign prostatic hyperplasia; b) relaxing urethral smooth muscle; or c) inhibiting contraction of prostate tissue; in a subject in need thereof, the effective ingredient of the said drug being any of the compounds described above.

DETAILED DESCRIPTION OF THE INVENTION

Representative compounds of the present invention exhibit high selectivity for the human alpha 1a adrenergic receptor. One implication of this selectivity is that these compounds display selectivity for lowering intraurethral pressure without substantially affecting diastolic blood pressure.

Representative compounds of this invention display submicromolar affinity for the human alpha 1a adrenergic receptor subtype while displaying at least ten-fold lower affinity for the human alpha1d and alpha1b adrenergic receptor subtypes, and many other G-protein coupled human receptors. Particular representative compounds of this invention exhibit nanomolar and subnanomolar affinity for the human alpha 1a adrenergic receptor subtype while displaying at least 30 fold lower affinity for the human alpha1d and alpha1b adrenergic receptor subtypes, and many other G-protein coupled human receptors. Preferred compounds of this invention exhibit Ki's for human alpha 1a adrenergic receptors which are more than 400 fold lower than for the human alpha1d or alpha 1adrenergic receptors, while exhibiting greater than 500 fold selectivity for the human alpha 1a adrenergic receptor over all other human G-protein coupled receptors tested (including serotonin, dopamine, alpha 2 adrenergic, beta adrenergic or muscarinic receptors).

These compounds are administered in dosages effective to antagonize the alpha 1a receptor where such treatment is needed, as in BPH. For use in medicine, the salts of the compounds of this invention refer to non-toxic "pharmaceutically acceptable salts." Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

Thus, representative pharmaceutically acceptable salts include the following:

Acetate, Benzenesulfonate, Benzoate, Bicarbonate, Bisulfate, Bitartrate, Borate, Bromide, Calcium, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isothionate, Lactate, Lactobionate, Laurate, Malate, Maleate, Mandelate, Mesylate, Methylbromide, Methylnitrate, Methylsulfate, Mucate, Napsylate, Nitrate, N-methylglucamine ammonium salt, Oleate, Oxalate, Pamoate (Embonate), Palmitate, Pantothenate, Phosphate/diphosphate, Polygalacturonate, Salicylate, Stearate, Sulfate, Subacetate, Succinate, Tannate, Tartrate, Teoclate, Tosylate, Triethiodide and Valerate.

The present invention includes within its scope prodrugs of the compounds of this invention. In general, such prodrugs will be functional derivatives of the compounds of this invention which are readily convertible in vivo into the required compound. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

Where the compounds according to the invention have at least one chiral center, they may accordingly exist as enantiomers. Where the compounds according to the invention possess two or more chiral centers, they may additionally exist as diastereoisomers. It is to be understood that all such isomers and mixtures thereof are encompassed within the scope of the present invention. Furthermore, some of the crystalline forms for compounds of the present invention may exist as polymorphs and as such are intended to be included in the present invention. In addition, some of the compounds of the present invention may form solvates with water (i.e., hydrates) or common organic solvents. Such solvates are also encompassed within the scope of this invention.

The term "alkyl" shall mean straight or branched chain alkanes of one to ten total carbon atoms, or any number within this range (i.e., methyl, ethyl, 1-propyl, 2-propyl, n-butyl, s-butyl, t-butyl, etc.).

The term "alkenyl" shall mean straight or branched chain alkenes of two to ten total carbon atoms, or any number within this range.

The term "aryl" as used herein, except where otherwise specifically defined, refers to unsubstituted, mono- or poly-substituted aromatic groups such as phenyl or naphthyl.

The term "cycloalkyl" shall mean cyclic rings of alkanes of three to eight total carbon atoms (i.e., cyclopropyl, cyclobutyl, cyclopentyl, cyclohexyl, cycloheptyl or cyclooctyl).

Whenever the term "alkyl" or "aryl" or either of their prefix roots appear in a name of a substituent (e.g., aralkoxyaryloxy) it shall be interpreted as including those limitations given above for "alkyl" and "aryl." Designated numbers of carbon atoms (e.g., $C_{1-10}$) shall refer independently to the number of carbon atoms in an alkyl or cyclic alkyl moiety or to the alkyl portion of a larger substituent in which alkyl appears as its prefix root.

The term "halogen" shall include iodine, bromine, chlorine and fluorine.

The term "substituted" shall be deemed to include multiple degrees of substitution by a named substitutent. The term "poly-substituted" as used herein shall include di-, tri-, tetra- and penta-substitution by a named substituent.

Where multiple substituent moieties are disclosed or claimed, the substituted compound can be independently substituted by one or more of the disclosed or claimed substituent moieties, singly or plurally.

The term heterocycle or heterocyclic ring, as used herein, represents an unsubstituted or substituted stable 5- to 7-membered monocyclic ring system which may be saturated or unsaturated, and which consists of carbon atoms and from one to three heteroatoms selected from N, O or S, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but is not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, and oxadiazolyl. Morpholino is the same as morpholinyl.

The term "thienyl," as used herein, refers to the group

The term "subject," as used herein refers to an animal, preferably a mammal, most preferably a human, who has been the object of treatment, observation or experiment.

The term "therapeutically effective amount" as used herein means that amount of active compound or pharmaceutical agent that elicits the biological or medicinal response in a tissue, system, animal or human that is being sought by a researcher, IC veterinarian, medical doctor or other clinician, which includes alleviation of the symptoms of the disease being treated.

The present invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

As used herein, the term "composition" is intended to encompass a product comprising the specified ingredients in the specified amounts, as well as any product which results, directly or indirectly, from combination of the specified ingredients in the specified amounts.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Where the processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F .W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The specificity of binding of compounds showing affinity for the $\alpha_{1a}$ receptor is shown by comparing affinity to membranes obtained from tranfected cell lines that express the $\alpha_{1a}$ receptor and membranes from cell lines or tissues known to express other types of alpha (e.g., $\alpha_{1d}$, $\alpha_{1b}$) or beta adrenergic receptors. Expression of the cloned human $\alpha_{1d}$, $\alpha_{1b}$, and $\alpha_{1a}$ receptors and comparison of their binding properties with known selective antagonists provides a rational way for selection of compounds and discovery of new compounds with predictable pharmacological activities. Antagonism by these compounds of the human alpha 1a adrenergic receptor subtype may be functionally demonstrated in anesthetized animals. These compounds may be used to increase urine flow without exhibiting orthostatic hypotensive effects.

The ability of compounds of the present invention to specifically bind to the $\alpha_{1a}$ receptor makes them useful for the treatment of BPH. The specificity of binding of compounds showing affinity for the $\alpha_{1a}$ a receptor is compared against the binding affinities to other types of alpha or beta adrenergic receptors. The human alpha adrenergic receptor of the 1-a subtype was recently identified, cloned and expressed as described in PCT International Application Publication Nos. WO94/08040, published Apr. 14, 1994 and WO 94/21660, published Sep. 29, 1994, each of which is hereby incorporated by reference. The cloned human $\alpha_{1a}$ receptor, when expressed in mammalian cell lines, is used to discover ligands that bind to the receptor and alter its function. Expression of the cloned human $\alpha_{1d}$, $\alpha_{1b}$, and $\alpha_{1a}$ receptors and comparison of their binding properties with known selective antagonists provides a rational way for selection of compounds and discovery of new compounds with predictable pharmacological activities.

Compounds of this invention exhibiting selective human $\alpha_{1a}$ adrenergic receptor antagonism may further be defined by counterscreening. This is accomplished according to methods known in the art using other receptors responsible for mediating diverse biological functions. [See e.g., PCT International Application Publication No. WO94/10989, published May 26, 1994; U.S. Pat. No. 5,403,847, issued Apr. 4, 1995]. Compounds which are both selective amongst the various human alpha1 adrenergic receptor subtypes and which have low affinity for other receptors, such as the alpha2 adrenergic receptors, the β-adrenergic receptors, the muscarinic receptors, the serotonin receptors, and others are particularly preferred. The absence of these non-specific activities may be confirmed by using cloned and expressed receptors in an analogous fashion to the method disclosed herein for identifying compounds which have high affinity for the various human alpha1 adrenergic receptors. Furthermore, functional biological tests are used to confirm the effects of identified compounds as alpha 1a adrenergic receptor antagonists.

The present invention also has the objective of providing suitable topical, oral, systemic and parenteral pharmaceutical formulations for use in the novel methods of treatment of the present invention. The compositions containing compounds of this invention as the active ingredient for use in the specific antagonism of human alpha 1a adrenergic receptors can be administered in a wide variety of therapeutic dosage forms in conventional vehicles for systemic administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as an alpha 1a antagonistic agent.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxy-ethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

Compounds of this invention may be administered in any of the foregoing compositions and according to dosage regimens established in the art whenever specific blockade of the human alpha 1a adrenergic receptor is required.

The daily dosage of the products may be varied over a wide range from 0.01 to 1,000 mg per adult human per day. For oral administration, the compositions are preferably provided in the form of tablets containing 0.01, 0.05, 0.1, 0.5, 1.0, 2.5, 5.0, 10.0, 15.0, 25.0, 50.0 and 100 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. An effective amount of the drug is ordinarily supplied at a dosage level of from about 0.0002 mg/kg to about 250 mg/kg of body weight per day. Preferably, the range is from about 0.001 to 100 mg/kg of body weight per day, and especially from about 0.001 mg/kg to 7 mg/kg of body weight per day. The compounds may be administered on a regimen of 1 to 4 times per day.

Compounds of this patent disclosure may be used alone at appropriate dosages defined by routine testing in order to obtain optimal antagonism of the human α1a adrenergic receptor while minimizing any potential toxicity. In addition, co-administration or sequential administration of other agents which alleviate the effects of BPH is desirable. Thus, in one embodiment, this includes administration of compounds of this invention and a human testosterone 5-α reductase inhibitor. Included with this embodiment are inhibitors of 5-alpha reductase isoenzyme 2. Many such compounds are now well known in the art and include such compounds as PROSCAR®, (also known as finasteride, a 4-Aza-steroid; see U.S. Pat. Nos. 4,377,584 and 4,760,071, for example, hereby incorporated by reference). In addition to PROSCAR®, which is principally active in prostatic tissue due to its selectivity for human 5α reductase isozyme 2, combinations of compounds which are specifically active in inhibiting testosterone 5-alpha reductase isozyme 1 and compounds which act as dual inhibitors of both isozymes 1 and 2, are useful in combination with compounds of this invention. Compounds that are active as 5α-reductase inhibitors have been described in WO93/23420, EP 0572166; WO 93/23050;

WO93/23038,; WO93/23049; WO93/23041; WO93/23040; WO93/23039; WO93/23376; WO93/23419, EP 0572165; WO93/23051, each of which is hereby incorporated by reference.

The dosages of the alpha 1a adrenergic receptor and testosterone 5-alpha reductase inhibitors are adjusted when combined to achieve desired effects. As those skilled in the art will appreciate, dosages of the 5-alpha reductase inhibitor and the alpha 1a adrenergic receptor antagonist may be independently optimized and combined to achieve a synergistic result wherein the pathology is reduced more than it would be if either agent were used alone. In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly.

Thus, in one preferred embodiment of the present invention, a method of treating BPH is provided which comprises administering to a subject in need of treatment any of the compounds of the present invention in combination with finasteride effective to treat BPH. The dosage of finasteride administered to the subject is about 0.01 mg per subject per day to about 50 mg per subject per day in combination with an $\alpha_{1a}$ antagonist. Preferably, the dosage of finasteride in the combination is about 0.2 mg per subject per day to about 10 mg per subject per day, more preferably, about 1 to about 7 mg per subject to day, most preferably, about 5 mg per subject per day.

For the treatment of benign prostatic hyperplasia, compounds of this invention exhibiting alpha 1a adrenergic receptor blockade can be combined with a therapeutically effective amount of a 5α-reductase 2 inhibitor, such as finasteride, in addition to a 5α-reductase 1 inhibitor, such as 4,7β-dimethyl-4-aza-5α-cholestan-3-one, in a single oral, systemic, or parenteral pharmaceutical dosage formulation. Alternatively, a combined therapy can be employed wherein the alpha 1a adrenergic receptor antagonist and the 5α-reductase 1 or 2 inhibitor are administered in separate oral, systemic, or parenteral dosage formulations. See, e.g., U.S. Pat. No.'s 4,377,584 and 4,760,071 which describe dosages and formulations for 5α-reductase inhibitors.

Abbreviations used in the instant specification, particularly the Schemes and Examples, are as follows:

BCE=bromochloroethane
Boc or BOC=t-butyloxycarbonyl
BOPCl=bis(2-oxo-3-oxazolidinyl)phosphinic chloride
Cbz-Cl=benzyloxycarbonyl chloride
DAST=diethylaminosulfurtrifluoride
DEAD=diethylazodicarboxylate
DMF=N,N-dimethylformamide
DMSO=dimethylsulfoxide
EDCl=1-(3-dimethylaminopropyl)-3-ethylcarbodiimide hydrochloride
Et=ethyl
Et$_3$N=triethylamine
EtOAc=ethyl acetate
EtOH=ethanol
FABLRMS=fast atom bombardment low resolution mass spectroscopy
HMPA=hexamethylphosporamide
HPLC=high performance liquid chromatography
HOAc=acetic acid
HOBt=1-hydroxy benzotriazole hydrate
i-PrOH=2-propanol i-Pr$_2$NEt=diisopropylethylamine
mCPBA=meta-chloroperbenzoic acid
Me=methyl
MeOH=methanol
NMR=nuclear magnetic resonance
PCTLC=preparative centrifugal thin layer chromatography
PEI=polyethylenimine
Ph=phenyl
RT=retention time
TEBAC=benzyltriethylammonium chloride
TFA=trifluoroacetic acid
THF=tetrahydrofuran
TLC=thin layer chromatography
TMS=trimethylsilyl The compounds of the present invention can be prepared readily according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Unless otherwise indicated, all variables are as defined above.

The preparation of 4,4-disubstituted piperidines 4 was accomplished via spiro annulation of substituted acetonitrile derivatives 1 with N-Boc bischloroethyl amine under basic conditions in good yields. The resulting nitrites could then be hydrolyzed and further elaborated or simply deprotected providing 4 and alkylated with N-Boc bromopropyl amine 5 (m=1) or bromoethyl amine (m=0) producing 6. Subsequent N-Boc deprotection afforded 7 and coupling with acetic acids or acetic acid chlorides derivatives 8a–k produced the desired amides 9a–k in modular fashion. Alternatively, the piperidine 4 was alkylated with the bromoalkyl amides 10a–k, which were prepared via coupling of the acetic acid derivatives 8a–k to bromopropyl or bromoethyl amine prior to alkylation.

SCHEME 1

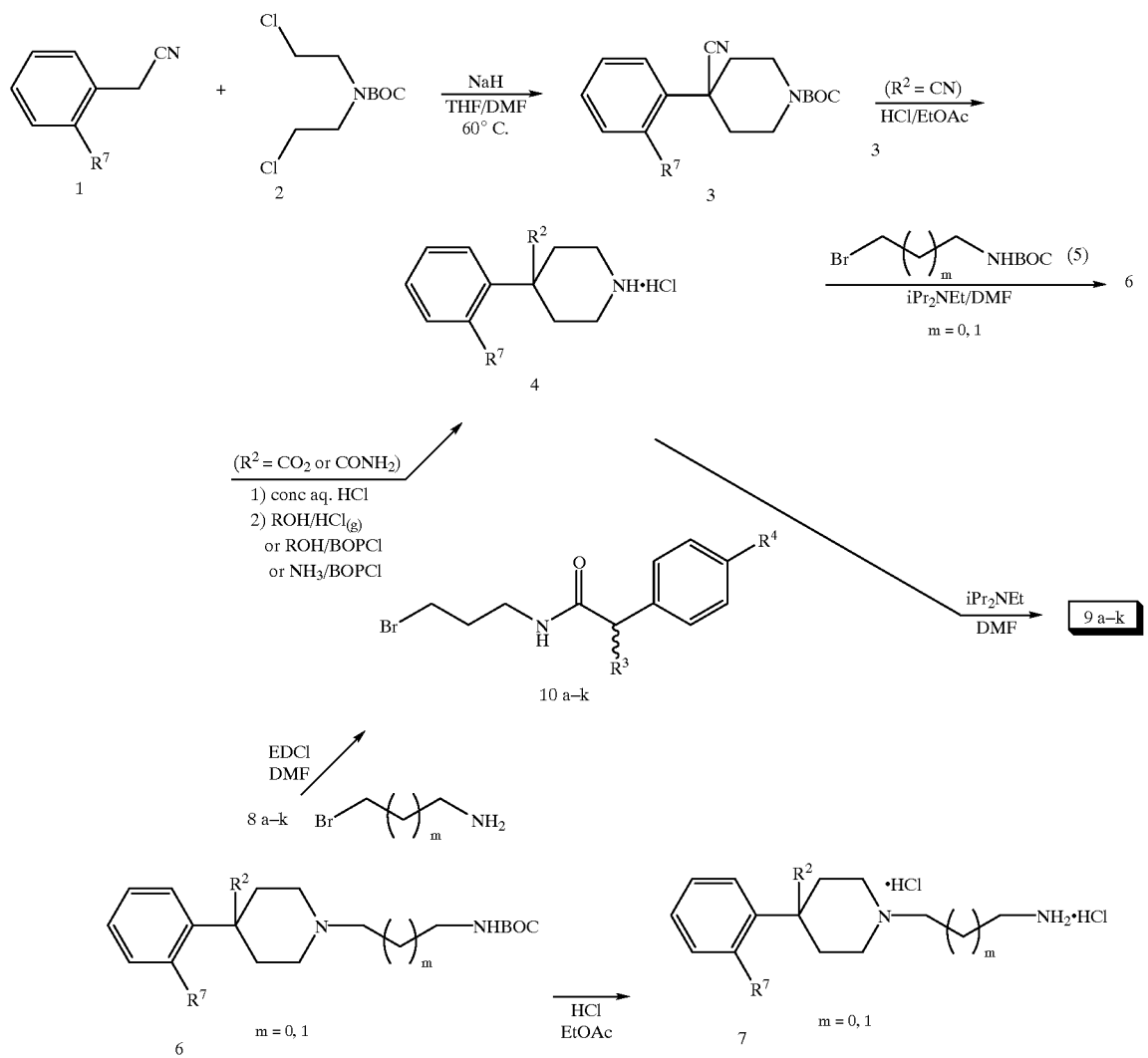

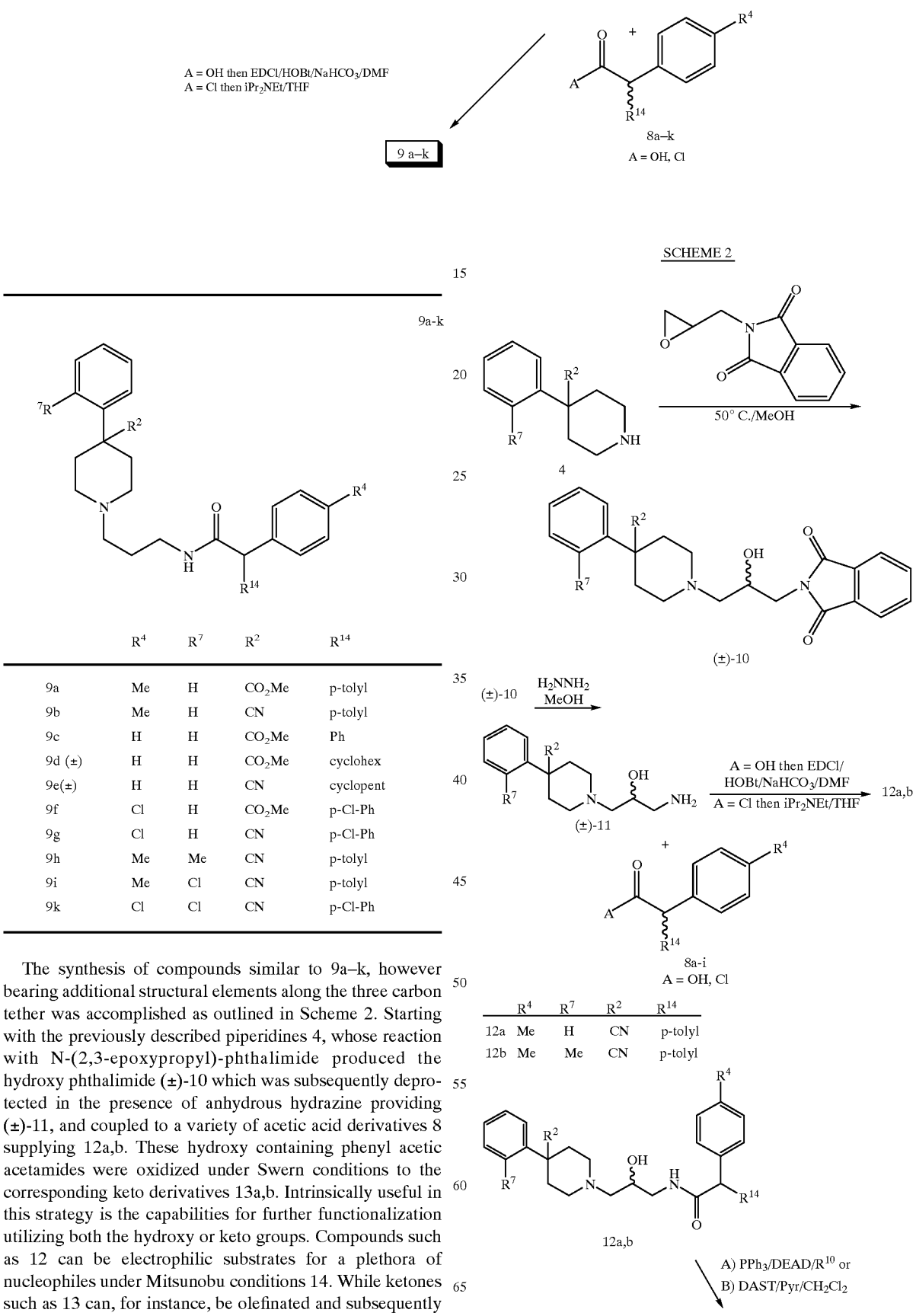

| | $R^4$ | $R^7$ | $R^2$ | $R^{14}$ |
|---|---|---|---|---|
| 9a | Me | H | CO₂Me | p-tolyl |
| 9b | Me | H | CN | p-tolyl |
| 9c | H | H | CO₂Me | Ph |
| 9d (±) | H | H | CO₂Me | cyclohex |
| 9e(±) | H | H | CN | cyclopent |
| 9f | Cl | H | CO₂Me | p-Cl-Ph |
| 9g | Cl | H | CN | p-Cl-Ph |
| 9h | Me | Me | CN | p-tolyl |
| 9i | Me | Cl | CN | p-tolyl |
| 9k | Cl | Cl | CN | p-Cl-Ph |

The synthesis of compounds similar to 9a–k, however bearing additional structural elements along the three carbon tether was accomplished as outlined in Scheme 2. Starting with the previously described piperidines 4, whose reaction with N-(2,3-epoxypropyl)-phthalimide produced the hydroxy phthalimide (±)-10 which was subsequently deprotected in the presence of anhydrous hydrazine providing (±)-11, and coupled to a variety of acetic acid derivatives 8 supplying 12a,b. These hydroxy containing phenyl acetic acetamides were oxidized under Swern conditions to the corresponding keto derivatives 13a,b. Intrinsically useful in this strategy is the capabilities for further functionalization utilizing both the hydroxy or keto groups. Compounds such as 12 can be electrophilic substrates for a plethora of nucleophiles under Mitsunobu conditions 14. While ketones such as 13 can, for instance, be olefinated and subsequently reduced 15.

| | $R^4$ | $R^7$ | $R^2$ | $R^{14}$ |
|---|---|---|---|---|
| 12a | Me | H | CN | p-tolyl |
| 12b | Me | Me | CN | p-tolyl |

-continued

Oxalyl chloride/
DMSO/Et₃N/CH₂Cl₂

14
for A) R¹⁰ = H or OR⁵
for B) R¹⁰ = F 13a,b

| | R⁴ | R⁷ | R² | R¹⁴ |
|---|---|---|---|---|
| 13a | Me | H | CN | p-tolyl |
| 13b | Me | Me | CN | p-tolyl |

1) R¹¹ = PPh₃ or Cp₂TiR¹¹₂
2) H₂/Pd—C

15
R¹¹ = CF₂ or CHF₂

The following examples are provided to further define the invention without, however, limiting the invention to the particulars of these examples.

EXAMPLE 1

Bis(2-chloroethyl)-N-(1,1-dimethylethoxy)carbonyl amine

A solution of N-(2,2'-bischloro)diethyl amine (23.0 g, 0.130 mol) and di-tert-butyl dicarbonate (28.8 g, 0.130 mol) in CH₂Cl₂ (150 mL) was treated with N,N-diisopropylethylamine (22.52 ml, 0.720 mol) at room temperature (1.5 h). The solvent was removed in vacuo and the residue was triturated with ether (300 ml). The ether solution was collected and concentrated in vacuo affording N-(2,2'-bischloro)-diethyl-N-(1,1-dimethylethoxy)carbonyl amine as a clear oil.

¹H NMR (CDCl₃, 400 MHz) d 3.65 (m, 8H), 1.52 (s, 9H) FABLRMS (3:1 mixture of dithiothreitol and dithioerythritol in MeOH) m/e 242 g/mole (M⁺+H, $C_{25}H_{29}N_2O_5SCl$= 242.2 g/mole.)

EXAMPLE 2

4-Cyano-N-(1,1-dimethylethoxy)carbonyl-4-(2-methylphenyl) piperidine

A solution of bis(2-chloroethyl)-N-(1,1-dimethylethoxy) carbonyl amine (1.438 g, 5.94 mmol) and 2-methylphenyl acetonitrile (600 mg, 3.96 mmol) in a 4:1 mixture of THF/DMF (15 mL) was treated with NaH (357.9 mg, 8.7 mmol) at 60° C. (3 d). The solvent was removed in vacuo, the residue dissolved in EtOAc (200 ml) and washed with saturated NaHCO₃ (50 ml), H₂O (2×50 ml), and saturated aqueous NaCl (50 ml), dried (Na₂SO₄) and concentrated in vacuo. PCTLC (SiO₂, 6 mm, 100% hexane) afforded 4-cyano-N-(1,1-dimethylethoxy)carbonyl-4-(2-methylphenyl) piperidine as a yellow/orange oil.

¹H NMR (CDCl₃, 400 MHz) d 7.25 (m,4H), 4.28 (br s, 2H), 3.28 (br t, 2H), 2.65 (s, 3H), 2.32 (d, 2H, J=13.0 Hz), 2.32 (dt 2H, J=4.1, 13.0 Hz), 1.48 (s, 9H).

HPLC (Vydac; C18; diameter=4.6 mm; length=15 cm; gradient=CH₃CN [0.1% TFA]—H₂O [0.1% TFA], 5%–95%, 95–5% over 20 min. 1.5 ml/min flow rate; RT=11.730 min; focus=215 nm; 75% pure.

EXAMPLE 3

4-Cyano-4-(2-methylphenyl)piperidine hydrochloride

A solution of EtOAc saturated with HCl (200 ml) was added to 4-cyano-N-(1,1-dimethylethoxy)carbonyl-4-(2-methylphenyl)piperidine (31 mg, 0.097 mmol). The resulting mixture was allowed to react for 1 hour at room temperature. The EtOAc was removed in vacuo affording 4-cyano-4-(2-methylphenyl)piperidine hydrochloride as a white solid.

¹H NMR (CD₃OD, 400 MHz) d 7.37 (m, 1H), 7.32 (m, 3H), 3.64 (dd, 2H, J=2.2, 11.4 Hz), 3.46 (t , 2H, J=13.5 Hz), 2.64 (m, 2H), 2.65 (s, 3H), 2.28 (t d, 2H, J=3.7 Hz, 13.5 Hz).

FABLRMS (3:1 mixture of dithiothreitol and dithioerythritol in MeOH) m/e 201 g/mole (M⁺+H, $C_{13}H_{16}N_2$=201.3 g/mole.)

HPLC (Vydac; C18; diameter=4.6 mm; length=15 cm; gradient=CH₃CN [0.1% TFA]—H₂O [10.1% TFA], 5%–95%, 95–5% over 20 min. 1.5 ml/min flow rate; RT=5.82 min; focus=215 nm; 100% pure.

Anal. Calcd for $C_{13}H_{16}N_2$. HCl and 0.30 H₂O and 0.25 CH₂Cl₂: C=60.42, H=6.93, N=10.64. Found: C=60.37, H=6.83, N=11.09.

EXAMPLE 4

4-(2-Chlorophenyl)-4-cyano-N-(1,1-dimethylethoxycarbonyl)piperidine

A solution of bis(2-chloroethyl)-N-1,1-dimethylethoxy) carbonyl amine (9.298 g, 38.4 mmol) and 2-chlorophenylacetonitrile (5.0 g, 32.0 mmol) in a 4:1 mixture of THF/DMF (15 mL) was treated with NaH (2.82 g, 70.4 mmol) at 60° C. (7 d). The solvent was removed in vacuo, the residue dissolved in EtOAc (200 ml) and washed with saturated NaHCO₃ (50 ml), H₂O (2×50 ml), and saturated aqueous NaCl (50 ml), dried (Na₂SO₄) and concentrated in vacuo. Trituration of the residue with 100% MeOH afforded 4-(2-chlorophenyl)-4-cyano-N-(1,1-dimethylethoxy) carbonyl piperidine as a white solid.

¹H NMR (CD₃OD, 400 MHz) d 7.53 (m, 2H), d 7.41 (m, 2H), 4.28 (br dd, 2H, J=13.4 Hz), 3.26 (m, 2H), 2.52 (dd, 2H, J=2.2, 11.2 Hz), 2.03 (dt, 2H, J=4.0, 9.2 Hz), 2.03 (s, 9H).

FABLRMS (3:1 mixture of dithiothreitol and dithioerythritol in MeOH) m/e 321 g/mole (M⁺+H, $C_{17}H_{21}N_2O_2Cl$= 320.8 g/mole.)

HPLC (Vydac; C18; diameter=4.6 mm; length=15 cm; gradient=CH₃CN [0.1% TFA]—H₂O [0.1% TFA], 5%–95%, 95–5% over 20 min. 1.5 ml/min flow rate; RT=11.70 min; focus=215 nm; 97.4% pure.

EXAMPLE 5

4-(2-Chlorophenyl)-4-cyanopiperidine hydrochloride

A solution of EtOAc saturated with HCl (200 ml) was added to 4-(2-chlorophenyl)-4-cyano-N-1,1- dimethylethoxycarbonyl)piperidine, (880 mg, 2.74 mmol). The resulting mixture was allowed to react for 1 hour at room temperature. The EtOAc was removed in vacuo affording 4-(2-Chlorophenyl)-4-cyanopiperidine hydrochloride as a white solid.

$^1$H NMR (CD$_3$OD, 400 MHz) d 7.53 (dd, 1H, J=2.0, 4.3 Hz), 7.5 (dd, 1H, J=2.0, 5.3 Hz), 7.40 (ddd, 2H, J=2.0, 6.0, 7.9 Hz), 3.14 (ddd, 4H, J=2.2, 10.8, 12.4 Hz), 2.51 (dd, 2H, J=2.2, 13.5 Hz), 2.00 (dt, 2H, J=3.4, 13.5 Hz).

FABLRMS (3:1 mixture of dithiothreitol and dithioerythritol in MeOH) m/e 221 g/mole (M$^+$+H, C$_{13}$H$_{16}$N$_2$=220.7 g/mole.)

HPLC (Vydac; C18; diameter=4.6 mm; length=1 5 cm; gradient=CH$_3$CN [0.1% TFA]—H$_2$O [0.1% TFA], 5%–95%, 95–5% over 20 min. 1.5 ml/min flow rate; RT=5.744 min; focus=215 nm; 99.04% pure.

Anal. Calcd for C$_{12}$H$_{13}$N$_2$Cl. HCl and 0.60 H$_2$O: C=62.26, H=6.18, N=12.10. Found: C=62.29, H=5.69, N=11.71.

EXAMPLE 6

4-(2-Chlorophenyl)-4-cyano-N-(3-[N-{1,1-dimethylethoxycarbonyl}]amino)propylpiperidine A solution of 4-(2-chlorophenyl)-4-cyanopiperidine hydrochloride (1 g, 3.90 mmol) and N-(3-bromopropyl)-N-(1,1-dimethylethoxy)carbonyl amine (924.3 mg, 3.90 mmol) in DMF (2 mL) was treated with N,N-diisopropylethylamine (5.056 ml, 29.64 mmole) at room temperature (2 d). The solvent was removed in vacuo, the residue dissolved in EtOAc (100 ml) and washed with saturated NaHCO$_3$ (30 ml), H$_2$O (2×30 ml), and saturated aqueous NaCl (30 ml), dried (Na$_2$SO$_4$) and concentrated in vacuo. PCTLC (SiO$_{2,}$ 6 mm, 10% MeOH; 90% CH$_2$Cl$_2$) afforded 4-(2-chlorophenyl)-4-cyano-N-[3-{N-(1,1-dimethyl-ethoxy)carbonyl}amino]propyl piperidine as an oil.

$^1$H NMR (CDCl$_3$, 400 MHz) d 7.53 (dd, 1H, J=1.7, 4.3 Hz), 7.51 (dd, 1H, J=2.1, 5.8 Hz), 7.40 (m, 2H), 3.11 (m, 4H), 2.54 (m, 6H), 2.11 (dd, 2H, J=2.0, 13.2 Hz), 1.72 (br t, 2H, J=6.5 Hz), 1.44 (s, 9H)

HPLC (Vydac; C18; diameter=4.6 mm; length=15 cm; gradient=CH$_3$CN [0.1% TFA]—H$_2$O [0.1% TFA], 5%–95%, 95–5% over 20 min. 1.5 ml/min flow rate; RT=7.935 min; focus=215 nm; 93.76% pure.

EXAMPLE 7

N-(3-amino)propyl-4-(2-chlorophenyl)-4-cyanopiperidine dihydrochloride

A solution of saturated HCl-EtOAc (200 ml) was added to 4-(2-Chlorophenyl)-4-cyano-N-(3-[N- {1,1-dimethylethoxycarbonyl}]amino)propylpiperidine (1.12 mg, 3.0 mmol). The resulting mixture was allowed to react for 1 hour at room temperature. The EtOAc was removed in vacuo affording 4-(2-chlorophenyl)-4-cyano-N-(3-amino) propyl-piperidine dihydrochloride as a white solid.

$^1$H NMR (CD$_3$OD, 400 MHz) d 7.57 (m, 2H), 7.46 (m, 2H), 3.89 (d br d, 2H, J=12.9 Hz), 3.43 (m, 4H), 3.1 (br dt, 2H, J=7.7 Hz), 2.93 (br d, 2H, J=15.4 Hz), 2.55 (br dt, 2H), 2.22 (m, 2H).

HPLC (Vydac; C18; diameter=4.6 mm; length=15 cm; gradient=CH$_3$CN [0.1% TFA]—H$_2$O [0.1% TFA], 5%–95%, 95–5% over 20 min. 1.5 ml/min flow rate; RT=5.36 min; focus=215 nm; 95.5% pure.

EXAMPLE 8

4-Cyano-N-(3-[N-{1,1-dimethylethoxycarbonyl}]amino)4-(2-methylphenyl)propylpiperidine A solution of 4-cyano-4-(2-methylphenyl) piperidine hydrochloride (1 g, 4.22 mmol) and N-(3-bromopropyl)-N-(1,1-dimethylethoxy)carbonyl amine (1.1 g, 4.65 mmol) in DMF (2 mL) was treated with N,N-diisopropylethylamine (5.5 ml, 32.07 mmole) at room temperature (4 d). The solvent was removed in vacuo, the residue was dissolved in EtOAc (100 ml) and washed with saturated NaHCO$_3$ (30 ml), H$_2$O (2×30 ml), and saturated aqueous NaCl (30 ml), dried (Na$_2$SO$_4$) and concentrated in vacuo. PCTLC (SiO$_2$, 6 mm, 10% MeOH; 90% CH$_2$Cl$_2$) afforded 4-cyano-4-(2-methylphenyl)-N-[3-{(1,1-dimethyl-ethoxy)carbonyl}amino]propyl piperidine as an oil.

$^1$H NMR (CDCl$_3$, 400 MHz) d 7.26 (m, 4H), 3.22 (d, 2H, J=6.0 Hz), 3.05 (br d, 2H, J=12.2 Hz), 2.65 (s, 3H), 2.54 (m, 4H), 2.31 (br dd, 2H, J=13.4 Hz), 2.06 (br dt, 2H, J=12.2 Hz), 1.71 (t, 2H, J=6.0 Hz), 1.44 (s, 9H).

FABLRMS (3:1 mixture of dithiothreitol and dithioerythritol in MeOH) m/e 358 g/mole (M$^+$+H, C$_{25}$H$_{29}$N$_2$O$_5$SCl= 357.6 g/mole.)

HPLC (Vydac; C18; diameter=4.6 mm; length=15 cm; gradient=CH$_3$CN [10.1% TFA]—H$_2$O [0.1% TFA], 5%–95%, 95–5% over 20 min. 1.5 ml/min flow rate; RT=7.982 min; focus=215 nm; 96.50% pure.

EXAMPLE 9

N-(3-Amino)propyl-4-cyano-4-(2-methylphenyl) piperidine dihydrochloride

A solution of EtOAc saturated with HCl (200 ml) was added to 4-cyano-N-(3-[N- {1,1-dimethylethoxycarbonyl}] amino)4-(2-methylphenyl)propylpiperidine (900 mg, 2.51 mmol). The resulting mixture was allowed to react room temperature (1 h). The EtOAc was removed in vacuo affording 4-cyano-4-(2-methylphenyl)-N-(3-amino) propyl-piperidine dihydrochloride as a white solid.

$^1$H NMR (CD$_3$OD, 400 MHz) d 7.35 (m, 4H), 3.87 (br d, 2H, J=12.5 Hz), 3.41 (m,4H), 3.11 (t, 2H, J=7.7 Hz), 2.74 (br dd, 2H, J=14.1 Hz), 2.66 (s, 3H), 2.51 (m, 2H), 2.23 (m, 2H)

HPLC (Vydac; C18; diameter=4.6 mm; length=15 cm; gradient=CH$_3$CN [0.1% TFA]—H$_2$O [0.1% TFA], 5%–95%, 95–5% over 20 min. 1.5 ml/min flow rate; RT=5.367 min; focus=215 nm; 95.96% pure).

EXAMPLE 10

2,2-Bis(4-chlorophenyl)-N-[3-(4-cyano-4-{2-methylphenyl}piperidin-1-yl)propyl]acetamide A solution of N-(3-amino)propyl-4-cyano-4-(2-methylphenyl)piperidine dihydrochloride (150 mg, 0.612 mmol) and 2,2-bis(4-chlorophenyl) acetic acid (169.62 mg, 0.612 mmol) in DMF (1 mL) was treated with 1-(3-dimethylaminopropyl)-3-ethylcarbodiimide hydrochloride (EDCI), (131.41 mg, 0.685 mmol), 1-hydroxy benzotriazole hydrate (HOBt), (95.26 mg, 0.685 mmole), and NaHCO$_3$ (257.04 mg, 3.06 mmol) at room temperature (18 h). The solvent was removed in vacuo, the residue was dissolved in EtOAc (200 ml) and washed with saturated NaHCO$_3$ (50 ml), H$_2$O (2×50 ml), and saturated aqueous NaCl (50 ml), dried (Na$_2$SO$_4$) and concentrated in vacuo. PCTLC (SiO$_2$, 4 mm, 1:1 hexane: EtOAc) afforded N-[4-cyano-4-(2-methylphenyl)piperidin-1-yl)propyl]-2-[bis(4-chlorophenyl)]acetamide as a white powder.

$^1$H NMR (CD$_3$OD, 400 MHz) d 7.30 (m, 12H), 4.93 (s, 1H), 3.30 (m, 2H), 2.61 (s, 3H), 2.45 (m, 4H), 2.33 (d br d, 2H, J=11.7 Hz), 1.98 (d d, 2H, J=9.8 Hz, 2.4 Hz), 1.74 (t, 2H, J=7.3 Hz).

FABLRMS (3:1 mixture of dithiothreitol and dithioerythritol in MeOH) m/e 520 g/mole (M$^+$+H, C$_{30}$H$_{31}$N$_3$OCl$_2$= 520.5 g/mole.)

HPLC (Vydac; C18; diameter=4.6 mm; length=15 cm; gradient=CH$_3$CN [0.1% TFA]—H$_2$O [0.1% TFA], 5%–95%, 95–5% over 20 min. 1.5 ml/min flow rate; RT=10.74 min; focus=215 nm; 98.1% pure.

Anal. Calcd for $C_{30}H_{31}N_3OCl_2$ and 0.90 $H_2O$: C=67.14, H=6.16, N=7.83. Found: C=67.14, H=5.87, N=8.04.

EXAMPLE 11

2,2-Bis(4-chlorophenyl)-N-[3-(4-{2-chlorophenyl}4-cyanopiperidin-1-yl)propylacetamide A solution of N-(3-amino)propyl-4-(2-chlorophenyl)-4-cyanopiperidine dihydrochloride (248.8 mg, 0.711 mmol) and 2,2-bis(4-chlorophenyl) acetic acid (200 mg, 0.711 mmol) in DMF (1 mL) was treated with 1-(3-dimethylaminopropyl)-3-ethylcarbodimide hydrochloride, (EDCI), (205.1 mg, 1.07 mmol), 1-hydroxybenzo-triazole hydrate, (HOBt), (148.7 mg, 1.07 mmole), and $NaHCO_3$ (298.62 mg, 3.55 mmol) at room temperature (18 h). The solvent was removed in vacuo, the residue dissolved in EtOAc (200 ml) and washed with saturated $NaHCO_3$ (50 ml), $H_2O$ (2×50 ml), and saturated aqueous NaCl (50 ml), dried ($Na_2SO_4$) and concentrated in vacuo. PCTLC ($SiO_2$, 4 mm, 1:1 hexane: EtOAc) afforded N-[4-(2-chlorophenyl)-4-cyanopiperidin-1-yl)propyl]-2-[bis(4-chlorophenyl)] acetamide as a white powder.

$^1$H NMR ($CD_3OD$, 400 MHz) d 7.51 (m, 2H), 7.40 (m, 2H), 7.30 (d d, 8H, J=7.5 Hz, 15.5 Hz), 4.93 (s, 1H), 3.21 (d, 2H, J=11.9 Hz), 3.02 (d, 2H, J=11.9), 2.48 (m, 6H), 2.01 (t, 2H, J=12.5 Hz), 1.74 (t, 2H, J=7.2 Hz),

FABLRMS (3:1 mixture of dithiothreitol and dithioerythritol in MeOH) m/e 542 g/mole ($M^+$+H, $C_{29}H_{28}N_3O_1Cl_3$= 541.9 g/mole.)

HPLC (Vydac; C18; diameter=4.6 mm; length=15 cm; gradient=$CH_3CN$ [0.1% TFA]—$H_2O$ [0.1% TFA], 5%–95%, 95–5% over 20 min. 1.5 ml/min flow rate; RT=10.68 min; focus=215 nm; 99.8% pure.

Anal. Calcd for $C_{29}H_{28}N_3OCl_3$ and 0.60 $H_2O$: C=63.13, H=5.33, N=7.62. Found: C=63.16, H=5.16, N=7.62.

EXAMPLE 12

2,2-Bis(4-methylphenyl)-N-[3-(4-cyano-4-{2-methylphenyl}piperidin-1-yl)propyl]acetamide A solution of 4-cyano-4-(2-methylphenyl)piperidine hydrochloride (200 mg, 0.845 mmol) and N-(3-bromopropyl)-2,2-bis(4-methylphenyl)carboxamide (365.35 mg, 1.014 mmol) in DMF (2 mL) was treated with N,N-diisopropylethylamine (0.588 ml, 6.42 mmol) at room temperature (18 h). The solvent was removed in vacuo, and the residue dissolved in EtOAc (200 ml) and washed with saturated $NaHCO_3$ (50 ml), $H_2O$ (2×50 ml), and saturated aqueous NaCl (50 ml), dried ($Na_2SO_4$) and concentrated in vacuo. PCTLC ($SiO_2$, 4 mm, 1:1 hexane: EtOAc) afforded N-[4-cyano-4-(2-methylphenyl)piperidin- 1-yl) propyl]-2-[bis(4-methyl-phenyl)]acetamide (200 mg, 487 mg theoretical, 41%) as a white powder.

$^1$H NMR ($CD_3OD$, 400 MHz) d 7.34 (d, 1H, J=1.5 Hz), 7.32 (t, 3H, J=1.8 Hz), 7.18 (m, 8H), 4.86 (s, 1H), 3.28 (d, 2H, J=6.6 Hz), 3.00 (br dd, 2H, J=12.8 Hz), 2.61 (s, 3H), 2.43 (m, 4H), 2.31 (m, 2H), 2.29 (s, 6H), 1.96 (dt, 2H, J=9.7 Hz, 2.4 Hz), 1.74 (m, 2H).

FABLRMS (3:1 mixture of dithiothreitol and dithioerythritol in MeOH) m/e 480 g/mole ($M^+$+H, $C_{32}H_{37}N_3O_1Cl_3$= 480.1 g/mole.)

HPLC (Vydac; C18; diameter=4.6 mm; length=15 cm; gradient=$CH_3CN$ [0.1% TFA]—$H_2O$ [0.1% TFA], 5%–95%, 95–5% over 20 min. 1.5 ml/min flow rate; RT=10.58 min; focus=215 nm; 97.0% pure.

Anal. Calcd for $C_{32}H_{37}N_3O$ and 0.40 $H_2O$: C=78.94, H=7.83 N=8.63. Found: C=78.98, H=7.71, N=8.69.

EXAMPLE 13

2,2-Bis(4-methylphenyl)-N-[3-(4-{2-chlorophenyl}4-cyanopiperidine-1-yl)propyl] acetamide A solution of 4-(2-chlorophenyl)-4-cyano-piperidine (200 mg, 0.910 mmol) and N-(3-bromopropyl)-2,2-di-(4-methylphenyl)carboxamide (36.24 mg, 1.092 mmol) in DMF (2 mL) was stirred for 18 hours. The solvent was removed in vacuo, the residue dissolved in EtOAc (200 ml) and washed with saturated $NaHCO_3$ (50 ml), $H_2O$ (2×50 ml), and saturated aqueous NaCl (50 ml), dried ($Na_2SO_4$) and concentrated in vacuo. PCTLC ($SiO_2$, 4 mm, 1:1 hexane: EtOAc) afforded N-[4-(2-chlorophenyl)-4-cyano-piperidin-1-yl)propyl]-2-[bis(4-methyl-phenyl)]-acetamide as a white powder.

$^1$H NMR ($CDCl_3$, 400 MHz: d 7.53 (ddd, 1 H, J=1.8, 2.8, 3.0 Hz), 7.33 (t, 3H, J=2.2 Hz), 7.14 (d, 4H, J=8.1 Hz), 7.08 (d, 4H, J=8.1 Hz), 4.83 (s, 1H), 3.42 (dd, 2H, J=1.5, 4.8 Hz), 3.05 (br d, 2H), 2.59 (br m, 4H), 2.46 (br dd, 2H, J=13.2 Hz), 2.29 (s, 6H), 2.02 (br m, 2H), 1.74 (br t, 2H).

FABLRMS (3:1 mixture of dithiothreitol and dithioerythritol in MeOH) m/e 500 g/mole ($M^+$+H, $C_{31}H_{34}N_3O_1Cl_1$= 500.1 g/mole.)

HPLC (Vydac; C18; diameter=4.6 mm; length=15 cm; gradient=$CH_3CN$ [0.1% TFA]—$H_2O$ [0.1% TFA], 5%–95%, 95–5% over 20 min. 1.5 ml/min flow rate; RT=10.339 min; focus=215 nm; 99.7% pure.

Anal. Calcd for $C_{31}H_{34}N_3O_1Cl$ and 0.65 $H_2O$: C=72.75 H=6.95 N=8.21 Found: C=72.75, H=6.84, N=8.21.

EXAMPLE 14

2,2-Bis(4-methylphenyl)-N-[3-({4-carboxymethyl}4-phenylpiperidin-1-yl)propyl] acetamide hydrochloride A solution of 3-amino-N-(4-carboxymethyl-4-phenyl) propylpiperidine dihydrochloride (139.41 mg, 0.416 mmol) and 2,2, di(4-methylphenyl) acetic acid (100 mg, 0.416 mmol) in DMF (1 mL) was treated with 1-(3-dimethylaminopropyl)-3-ethylcarbodimide hydrochloride, (EDCI), (119.7 mg, 0.624 mmol), 1-hydroxy benzotriazole hydrate, (HOBt), (86.72 mg, 0.624 mmole), and $NaHCO_3$ (34.95 mg, 0.416 mmol) at room temperature (18 h). The solvent was removed in vacuo, the residue dissolved in EtOAc (200 ml) and washed with saturated $NaHCO_3$ (50 ml), $H_2O$ (2×50 ml), and saturated aqueous NaCl (50 ml), dried ($Na_2SO_4$) and concentrated in vacuo. PCTLC ($SiO_2$, 4 mm, 10% MeOH: 90% $CH_2Cl_2$) afforded N-[4-carboxyethyl-4-phenyl)piperidin-1-yl) propyl]-2-[bis(4-methylphenyl)]acetamide as a white powder.

$^1$H NMR ($CD_3OD$, 400 MHz) d 7.35 (m, 3H), 7.25 (m, 1H), 7.1 1(m, 8H), 4.93 (s, 1H), 3.63 (s, 3H), 3.26 (m,2H), 2.77 (m, 2H), 2.52 (br d, 2H, 12.3 Hz), 2.30 (s, 6H), 2.28 (br d, 2H, 12.3 Hz), 2.1 8 (t, 2H, 7.3 Hz), 1.98 (br t, 2H), 1.74 (t, 2H, J=7.3 Hz).

FABLRMS (3:1 mixture of dithiothreitol and dithioerythritol in MeOH) m/e 499 g/mole ($M^+$+H, $C_{32}H_{38}N_2O3$=498.7 g/mole.)

HPLC (Vydac; C18; diameter=4.6 mm; length=15 cm; gradient=$CH_3CN$ [0.1% TFA]—$H_2O$ [0.1% TFA], 5%–95%, 95–5% over 20 min. 1.5 ml/min flow rate; RT=8.66 min; focus=215 nm; 99.2% pure).

Anal. Calcd for $C_{32}H_{39}N_2O_3Cl_1$ and 0.05 $H_2O$ and 0.25 $CH_2Cl_2$: C=69.51, H=7.16, N=5.03. Found: C=69.53, H=6.91, N=5.22.

EXAMPLE 15

2,2-Bis(4-chlorophenyl)-N-[3-(4-cyano-4-phenylpiperidin-1-yl)propylacetamide A solution of 4-cyano-4-phenyl-N-(3-amino)propyl-piperidine dihydrochloride (104.5 mg, 0.3557 mmol, 1.2 equiv) and 2,2-bis(4-chlorophenyl) acetic acid (100.0 mg, 0.3557 mmol, 1.0 equiv) in anhydrous DMF (1.5 mL) at 25° C. was treated with EDCI (82 mg, 0.42684 mmol, 1.2 equiv), HOBt (58 mg, 0.42684 mmol, 1.2 equiv), and NaHCO₃ (150 mg, 1.7785 mmol, 5 equiv) under Ar. The resulting mixture was stirred at 25° C. (24 h) and quenched by the addition of H₂O (15 mL) and CH₂Cl₂ (10 mL). The aqueous phase was extracted with CH₂Cl₂ (2×10 mL) and the combined organic extracts were washed with H₂O (2×15 mL) and saturated aqueous NaCl (1×15 mL), dried (Na₂SO₄), and concentrated in vacuo affording a white foam which solidified upon standing. PCTLC (SiO₂, 2 mm, 0–10% CH₃OH—CH₂Cl₂ afforded the desired product.

¹H NMR (CD₃OD, 400 MHz) d 7.4–7.6 (m, 5H), 7.25–7.40 (m, 8H), 4.99 (s, 1H), 3.70 (br s, 2H), 3.37 (br m, 3H), 3.21 (br m, 3H), 2.48 (br d, 2H, J=13.5 Hz), 2.35 (br m, 2H), 2.02 (br m, 2H).

HPLC (Vydac; C18; diameter=4.6 mm; length=15 cm; gradient=CH₃CN [0.1% TFA]—H₂O [0.1% TFA], 5%–95%, 95–5% over 20 min. 1.5 ml/min flow rate; RT=10.66 min; focus=215 nm; 97.6% pure).

Anal. Calcd for C₂₉H₂₉N₃OCl₂.HCl and 0.55 DMF and 0.85 CH₂Cl₂: C=57.73, H=5.47, N=7.57. Found: C=57.82, H=5.46, N=7.66.

EXAMPLE 16

2,2-Bis(4-methylphenyl)-N-[3-(4-cyano-4-phenylpiperidin-1-yl)propyl]acetamide hydrochloride A solution of 4-cyano-4-phenyl piperidine hydrochloride (100 mg, 0.449 mmol, 1.0 equiv) in anhydrous/degassed DMF (1.0 mL) at 25° C. was treated with N-(3-bromopropyl)-2,2-di-(4-methylphenyl)carboxamide (178 mg, 0.449 mmol, 1.1 equiv), and iPr2NEt (157 µL, 0.9878 mmol, 2.2 equiv) under Ar. The resulting mixture was stirred at 25° C. (24 h) and quenched by the addition of saturated aqueous NaHCO₃ (5.0 mL) and CH₂Cl₂ (5.0 mL). The aqueous phase was extracted with CH₂Cl₂ (2×5.0 mL) and the combined organic extracts were washed with water (3×10 mL) and saturated aqueous NaCl (1×10 mL), dried (Na₂SO₄), and concentrated in vacuo. Chromatography (PCTLC, SiO₂, 2 min, 0–10% CH₃OH—CH₂Cl₂) afforded the alkylated product, which was concentrated in vacuo, dissolved in dry EtOAc (2.0 mL), cooled to 0° C. and treated with saturated HCl-EtOAc (5 mL), concentrated in vacuo after ~1 h, triturated with dry ether (3×2.0 mL) and thoroughly dried.

¹H NMR (CDCl₃, 400 MHz) d 7.41–7.47 (m, 3H), 7.37 (m, 2H), 7.11 (m, 8H) 6.40 (br s, 1H), 4.82 (s, 1H), 3.38 (dd, 2H, J=5.9, 12.3 Hz), 2.93 (br m, 2H), 2.45 (br m, 4H), 2.29 (s, 6H, 2.04 (br dd, 2H, J=12.4 Hz), 1.93 (br m, 2H), 1.72 (br m, 2H).

HPLC (Vydac; C18; diameter=4.6 mm; length=15 cm; gradient=CH₃CN [0.1% TFA]—H₂O [0.1% TFA], 5%–95%, 95–5% over 20 min. 1.5 ml/min flow rate; RT=9.86 min; focus=215 nm; 98.2% pure).

Anal. Calcd for C₃₁ H₃₅N₃O.HCl: C=74.15, H=7.23, N=8.37 Found: C=74.18, H=7.23, N=8.03.

EXAMPLE 17

1-(tert-Butoxycarbonylamino)-3-bromopropane

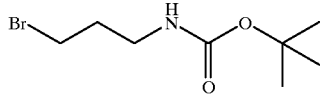

A suspension of 3-bromopropylamine hydrobromide (38.0 g, 0.174 mole) and di-tert-butyldicarbonate (41.6 g, 0.191 mole) in dichloromethane(250 mL) was treated with diisopropylethylamine (52 mL, 0.298 mole) at room temperature. The resulting mixture was stirred at room temperature overnight. The mixture was diluted with 100 mL of 1 N HCl. The aqueous layer was extracted with two additional 100 mL portions of dichloromethane and the combined organic extracts were washed with brine, dried over Na₂SO₄, and concentrated under reduced pressure. Flash chromatography on silica gel (10% EtOAc/hexane) afforded the title compound (16).

EXAMPLE 18

N-(2-cyanophenyl)-N'-(3-tert-butoxycarbonylaminopropyl)-piperazine and N-(2-amidophenyl)-N'-(3-tert-butoxycarbonylaminopropyl)-piperazine

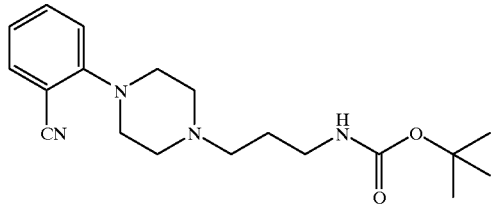

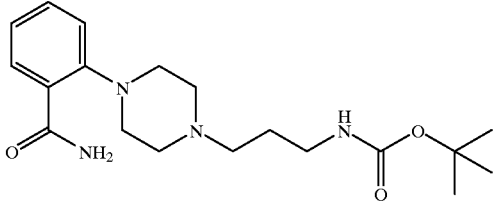

A solution of N-(2-cyanophenyl)-piperazine/N-2-amidophenyl)-piperazine (528 mg, 2.57 mmol) and 1-(tert-butoxycarbonylamino)- 3-bromopropane (16, 657 mg, 2.76 mmol) in DMF (3 mL) was treated with diisopropylethylamine (524 µL, 3.00 mmol) at room temperature. The resulting mixture was stirred at room temperature overnight. The solvent was removed in vacuo and the residue dissolved in dichloromethane and potassium carbonate solution. The aqueous layer was extracted with two additional portions of dichloromethane and the combined organic extracts were washed with brine, dried over Na₂SO₄, and concentrated under reduced pressure. The crude mixture was used directly.

EXAMPLE 19

N-(2-cyanophenyl)-N'-(3-aminopropyl)-piperazine and N-(2-amidophenyl)-N'-(3-aminopropyl)-piperazine (3)

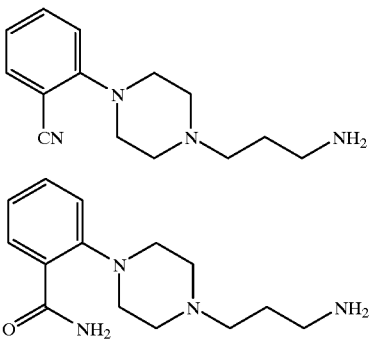

A solution of the crude mixture from Example 18 (930 mg, 2.50 mmol) in ethyl acetate (20 mL) was cooled to 0° C. and treated with HCl gas for 5 min. The mixture was stirred at room temperature (3 h). The solvent was removed in vacuo and the residue dissolved in dichloromethane and sodium bicarbonate solution. The aqueous layer was extracted with two additional portions of dichloromethane and the combined organic extracts were washed with brine, dried over $Na_2SO_4$, and concentrated under reduced pressure. The crude mixture was used directly.

EXAMPLE 20

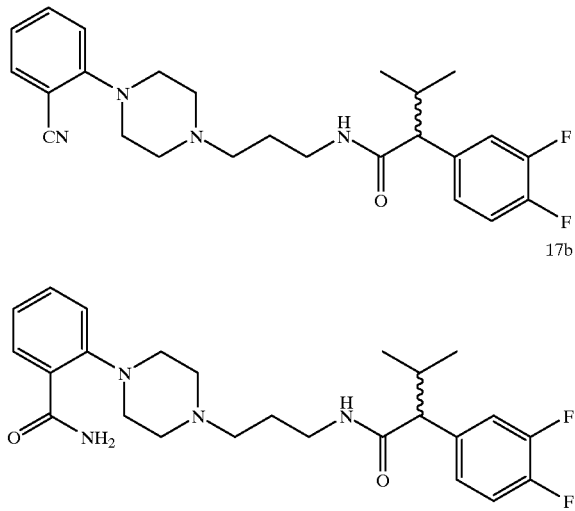

A solution of the crude mixture from Example 19 (319 mg, 1.21 mmol), 2-(3,4-difluorophenyl)-3-methylbutanoic acid (239 mg, 1.11 mmol), EDCI (238 mg, 1.24 mmol), and HOBT (166 mg, 1.23 mmol) in DMF (3 mL) was treated with diisopropylethylamine (580 µL, 3.33 mmol) at room temperature. The resulting mixture was stirred at room temperature overnight. The solvent was removed in vacuo PCTLC (SiO$_2$, 4 mm, 10% EtOH; 90% CHCl$_3$) afforded 17a and 17b as the hydrochloride salt after treatment with methanolic HCl. 17a:

$^1$H NMR (CDCl$_3$, 400 MHz) consistant with assigned structure.

FABLRMS m/e 459 g/mole (M$^+$+H, $C_{25}H_{32}F_2N_4O_2$=459 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) RT=8.075 min; focus= 215 nm; 93% pure.

Anal. Calcd for $C_{25}H_{32}F_2N_4O_2 \cdot 0.40$ H$_2$O: C=64.46, H=7.10, N=12.03. Found: C=64.53, H=7.12, N=11.81. 17b:

$^1$H NMR (CDCl$_3$, 400 MHz) consistant with assigned structure.

FABLRMS m/e 441 g/mole (M$^+$+H, $C_{25}H_{30}F_2N_4O$=441 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) RT=9.013 min; focus=215 nm; 99% pure.

Anal. Calcd for $C_{25}H_{30}F_2N_4O \cdot 0.60$ HCl$\cdot 1.35$ H$_2$O: C=61.69, H=6.90 N=11.51. Found: C=61.71, H=6.91, N=11.22.

EXAMPLE 21

N-(3-tert-butoxycarbonylaminopropyl)-4-cyano-4-phenylpiperidine (6)

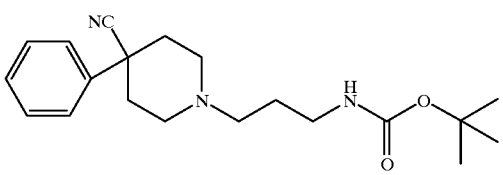

A solution of 4-cyano-4-phenylpiperidine (9.52 g, 42.7 mmol) and 1-(tert-butoxycarbonylamino)-3-bromopropane (16, 10.58 g, 44.4 mmol) in DMF (70 mL) was treated with diisopropylethylamine (18.6 mL, 107 mmol) at room temperature. The resulting mixture was stirred at room temperature (3 d). The solvent was removed in vacuo and the residue dissolved in dichloromethane and sodium bicarbonate solution. The aqueous layer was extracted with two additional portions of dichloromethane and the combined organic extracts were washed with brine, dried over Na$_2$SO$_4$, and concentrated under reduced pressure. Flash chromatography on silica gel (10% methanol/dichloromethane) afforded the title compound (18).

$^1$H NMR (CDCl$_3$, 400 MHz) consistant with assigned structure.

FABLRMS m/e 344 g/mole (M$^+$+H, $C_{20}H_{29}N_3O_2$=344 g/mole.)

HPLC (Vydac; C18; diameter=4.6 mm; length=150 mm; gradient=H$_2$O [10% H$_3$PO$_4$]—CH$_3$CN, 95%–5%, 5%–95%, over 16 minutes, 2 ml/min flow rate) RT=7.46 min; focus= 215 nm; 99% pure.

EXAMPLE 22

N-(3-aminopropyl)-4-cyano-4-phenylpiperidine (19)

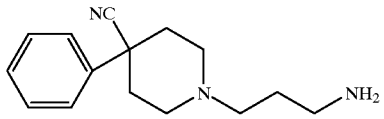

A solution of 18 (13.29 g, 38.69 mmol) in ethyl acetate (300 mL) was treated with sat'd HCl/EtOAc solution (250 mL) at room temperature. The mixture was stirred at room temperature (3 h). The solvent was removed in vacuo and the residue dissolved in ethyl acetate and sodium carbonate solution. The organic extract was washed with brine, dried over Na$_2$SO$_4$, and concentrated under reduced pressure to afford the title compound (19). The crude product was used directly.

FABLRMS m/e 244 g/mole (M$^+$+H, C$_{15}$H$_{21}$N$_3$=244 g/mole.)

EXAMPLE 23

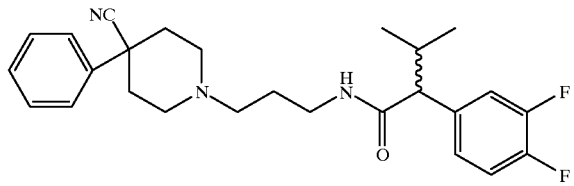

A solution of 19 (135 mg, 0.426 mmol), 2-(3,4-difluorophenyl)-3-methylbutanoic acid (72 mg, 0.336 mmol), EDC$_1$ (78 mg, 0.406 mmol), and HOBT (55 mg, 0.407 mmol) in DMF (1 mL) was treated with diisopropylethylamine (350 μL, 2.01 mmol) at room temperature. The resulting mixture was stirred at room temperature overnight. The solvent was removed in vacuo. PCTLC (SiO$_2$, 4mm, 10% EtOH; 90% CHCl$_3$) afforded 20 as the hydrochloride salt after treatment with methanolic HCl.

$^1$H NMR (CDCl$_3$, 400 MHz) consistant with assigned structure.

FABLRMS m/e 440 g/mole (M$^+$+H, C$_{26}$H$_{31}$F$_2$N$_3$O=440 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) RT=9.675 min; focus=215 nm; 100% pure.

Anal. Calcd for C$_{26}$H$_{31}$F$_2$N$_3$O.1.00 HCl.1.00 H$_2$O: C=63.21, H=6.94, N=8.51. Found: C=63.21, H=6.93, N=857.

EXAMPLE 24

Bis-p-tolylacetic acid, methyl ester (21)

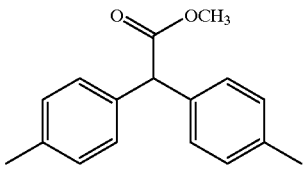

A solution of di-p-tolylacetic acid (4.90 g, 20.4 mmol) in methanol was treated with sat'd HCl/MeOH solution at room temperature. The mixture was stirred at room temperature (3 h). The solvent was removed in vacuo and the residue dissolved in dichloromethane and sodium bicarbonate solution. The aqueous layer was extracted with two additional portions of dichloromethane and the combined organic extracts were washed with brine, dried over Na$_2$SO$_4$, and concentrated under reduced pressure to afford the title compound (21). The crude product was used directly.

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) RT=12.672 min; focus=215 nm; 98% pure.

EXAMPLE 25

Di-p-tolylhydroxyacetic acid methyl ester (22)

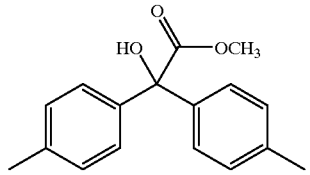

A suspension of NaH (255 mg, 10.6 mmol) in tetrahydrofuran (50 mL) was cooled to 0° C. and treated with a solution of 21 (2.29 g, 9.00 mmol) in tetrahydrofuran. The cooling bath was removed and DMF (1 mL) was added to the reaction. The resulting mixture was stirred at room temperature overnight. The mixture was treated with TMS-Cl (10 mL of 1M THF solution) and stirred at room temperature (2 h). The reaction was treated with solid MCPBA (85%, 3.49 g, 17.2 mmol) and stirred at room temperature overnight. The reaction was quenched with tetrabutylammonium fluoride and diluted with ethyl acetate and water. The aqueous layer was extracted with two additional portions of ethyl acetate and the combined organic extracts were washed with brine, dried over Na$_2$SO$_4$, and concentrated under reduced pressure. Flash chromatography on silica gel (dichloromethane/hexane) afforded the title compound (22).

$^1$H NMR (CDCl$_3$, 400 MHz) consistant with assigned structure.

EXAMPLE 26

Bis-p-tolylhydroxyacetic acid (23)

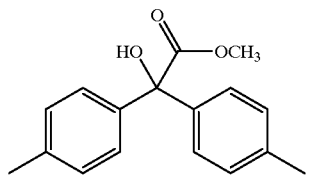

A solution of 22 (613 mg, 2.26 mmol) in methanol (75 mL) was treated with 1 N NaOH (10 mL) at room temperature. The mixture was stirred at room temperature overnight. The mixture was neutralized with 1 N HCl and the solvent was removed in vacuo. The residue was dissolved in dichloromethane and 1 N HCl solution. The aqueous layer was extracted with two additional portions of dichloromethane and the combined organic extracts were washed with brine, dried over Na$_2$SO$_4$, and concentrated under reduced pressure to afford the title compound (23). The crude product was used directly.

EXAMPLE 27

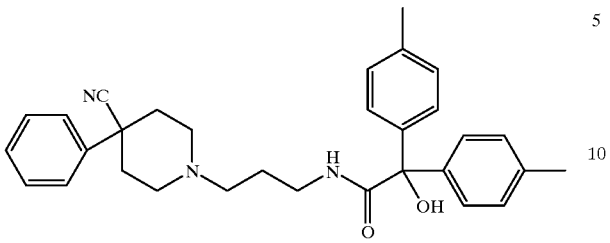

24

A solution of 23 (275 mg, 1.07 mmol), 19 (429 mg, 1.35 mmol), EDCI (226 mg, 1.17 mmol), and HOBT (157 mg, 1.16 mmol) in DMF (1 mL) was treated with diisopropylethylamine (860 μL, 4.94 mmol) at room temperature. The resulting mixture was stirred at room temperature overnight. The solvent was removed in vacuo. The residue was dissolved in dichloromethane and sodium bicarbonate solution. The aqueous layer was extracted with one additional portion of dichloromethane and the combined organic extracts were washed with brine, dried over $Na_2SO_4$, and concentrated under reduced pressure. PCTLC ($SiO_2$, 4mm, 10% EtOH; 90% $CHCl_3$) afforded 24 as the hydrochloride salt after treatment with methanolic HCl.

$^1$H NMR ($CDCl_3$, 400 MHz) consistant with assigned structure.

FABLRMS m/e 482 g/mole ($M^+$+H, $C_{31}H_{35}N_3O_2$=482 g/mole.)

HPLC (Vydac; C18; diameter=4.6 mm; length=150 mm; gradient=$H_2O$ [0.1% $H_3PO_4$]—$CH_3CN$, 95%–5%, 5%–95%, over 16 minutes, 2 ml/min flow rate) RT=9.941 min; focus=215 nm; 98% pure.

Anal. Calcd for $C_{31}H_{35}N_3O_2$.1.20 HCl.0.30 DMF: C=70.00, H=7.05, N=8.45. Found: C=69.93, H=7.25, N=8.42.

EXAMPLE 28

N-(3-tert-butoxycarbonylaminopropyl)-4-cyano-4-(o-tolyl)piperidine (25)

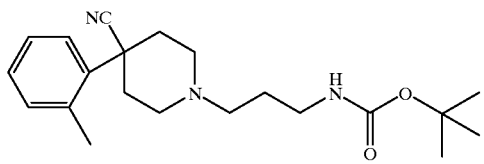

A solution of 4-cyano-4-(o-tolyl)piperidine (5.00 g, 24.9 mmol) and 1-(tert-butoxycarbonylamino)-3-bromopropane (16, 6.55 g, 27.5 mmol) in DMF (100 mL) was treated with diisopropylethylamine (4.50 mL, 25.8 mmol) at room temperature. The resulting mixture was stirred at room temperature (3 d). The solvent was removed in vacuo and the residue dissolved in dichloromethane and sodium bicarbonate solution. The aqueous layer was extracted with two additional portions of dichloromethane and the combined organic extracts were washed with brine, dried over $Na_2SO_4$, and concentrated under reduced pressure. Flash chromatography on silica gel (5% methanol/dichloromethane) afforded the title compound (25).

EXAMPLE 29

N-(3-aminopropyl)-4-cyano-4-(o-tolyl)piperidine (26)

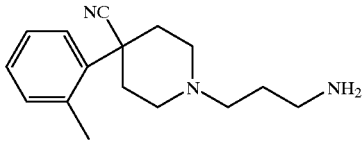

A solution of 25 (7.90 g, 22.0 mmol) in ethyl acetate (200 mL) was cooled to 0° C. and treated with sat'd HCl/EtOAc solution (200 mL). The mixture was stirred at room temperature (1 h). The solvent was partially removed in vacuo and the mixture diluted with ethyl acetate and sodium carbonate solution. The aqueous layer was extracted with two additional portions of ethyl acetate and three portions of dichloromethane. The combined organic extracts were washed with brine, dried over $Na_2SO_4$, and concentrated under reduced pressure to afford the title compound (26). The crude product was used directly.

EXAMPLE 30

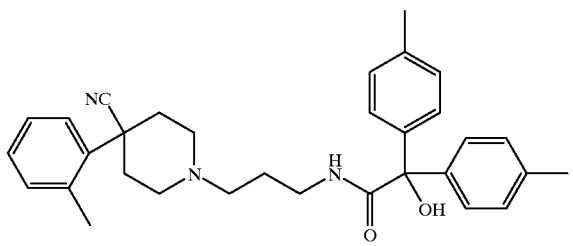

27

A solution of 23 (160 mg, 0.624 mmol), 26 (250 mg, 0.971 mmol), EDCI (189 mg, 0.985 mmol), and HOBT (134 mg, 0.991 mmol) in DMF (1 mL) was treated with diisopropylethylamine (600 μL, 3.44 mmol) at room temperature. The resulting mixture was stirred at room temperature overnight. The solvent was removed in vacuo. The residue was dissolved in dichloromethane and sodium bicarbonate solution. The aqueous layer was extracted with two additional portions of dichloromethane and the combined organic extracts were washed with brine, dried over $Na_2SO_4$, and concentrated under reduced pressure. PCTLC ($SiO_2$, 4mm, 10% EtOH; 90% $CHCl_3$) afforded 27 as the hydrochloride salt after treatment with methanolic HCl.

$^1$H NMR ($CDCl_3$, 400 MHz) consistant with assigned structure.

FABLRMS m/e 496 g/mole ($M^+$+H, $C_{32}H_{37}N_3O_2$=496 g/mole.)

HPLC (Vydac; C18; diameter=4.6 mm; length=150 mm; gradient=$H_2O$ [0.1% $H_3PO_4$]—$CH_3CN$, 95%–5%, 5%–95%, over 16 minutes, 2 ml/min flow rate) RT=10.389 min; focus=215 nm; 95% pure.

Anal. Calcd for $C_{32}H_{37}N_3O_2$.1.55 HCl.0.30 DMF: C=68.82, H=7.14, N=8.05. Found: C=68.81, H=7.02, N=7.99.

EXAMPLE 31

Cuprate of 3,4-difluorophenyl magnesium bromide

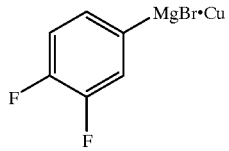

A solution of 1-bromo-3,4-difluorobenzene (10.0 g, 51.0 mmol) in ethyl ether (10 mL) was treated with solid magnesium turnings (1.22 g, 50.1 mmol) at room temperature. The resulting mixture was diluted with ethyl ether (50 mL) and stirred at room temperature (30 min). The mixture was cooled to 0° C. and treated with copper bromide-dimethyl sulfide complex (5.24 g, 25.5 mmol) with stirring (1 h). The crude reaction mixture was used directly.

EXAMPLE 32

Bis-3,4-difluorophenylketone (28)

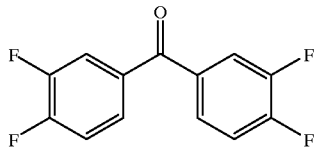

A solution of 3,4-difluorobenzoyl chloride (2.206 g, 12.5 mmol) in ethyl ether (20 mL) was cooled to 0° C. and treated with the crude mixture from Example 31 (25 mmol). The reaction was stirred at 0° C. (3 h) and quenched with aqueous ammonium chloride solution. The resulting mixture was stirred at room temperature overnight. The aqueous layer was extracted with two additional portions of ethyl ether and the combined organic extracts were washed with brine, dried over $Na_2SO_4$, and concentrated under reduced pressure. Flash chromatography on silica gel (5% EtOAc/hexane) afforded the title compound (28).

FABLRMS m/e 255 g/mole ($M^++H$, $C_{13}H_6F_4O$=255 g/mole.)

HPLC (Vydac; C18; diameter=4.6 mm; length=150 mm; gradient=$H_2O$ [0.1% $H_3PO_4$]—$CH_3CN$, 95%–5%, 5%–95%, over 16 minutes, 2 ml/min flow rate) RT=11.55 min; focus=215 nm; 86% pure.

EXAMPLE 33

TMS ether of cyanohydrin of 28 (29)

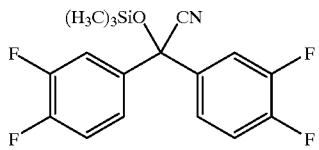

A solution of 28 (2.77 g, 10.9 mmol) and zinc iodide (372 mg, 1.16 mmol) in dichloromethane (30 mL) was treated with TMS-CN (3.06 mL, 22.9 mmol) at room temperature. The resulting mixture was stirred at room temperature overnight. The solvent was removed in vacuo to afford the title compound (29). The crude product was used directly.

EXAMPLE 34

Bis-3,4-difluorophenylhydroxyacetic acid (30)

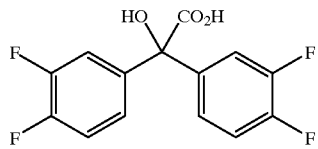

A solution of 29 (3.80 g, 10.7 mmol) in 12 M HCl (100 mL) was heated to reflux (2 h). The resulting mixture was cooled and extracted with two portions of dichloromethane. The combined organic extracts were washed with brine, dried over $Na_2SO_4$, and concentrated under reduced pressure. PCTLC ($SiO_2$, 6 mm, 1% AcOH; 10% EtOH; 89% $CHCl_3$) afforded 30.

$^1$H NMR ($CDCl_3$, 400 MHz) consistant with assigned structure.

EXAMPLE 35

31

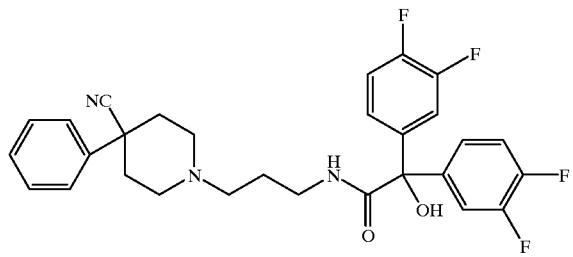

A solution of 19 (644 mg, 2.64 mmol), 30 (575 mg, 1.91 mmol), EDCI (383 mg, 1.99 mmol), and HOBT (270 mg, 1.99 mmol) in DMF (3 mL) was treated with diisopropylethylamine (700 μL, 4.01 mmol) at room temperature. The resulting mixture was stirred at room temperature (3 d). The solvent was removed in vacuo. PCTLC ($SiO_2$, 4 mm, 10% EtOH; 90% $CHCl_3$) afforded 31 as the hydrochloride salt after treatment with methanolic HCl.

$^1$H NMR ($CDCl_3$, 400 MHz) consistant with assigned structure.

FABLRMS m/e 526 g/mole ($M^++H$, $C_{29}H_{27}F_4N_3O_2$=526 g/mole.)

HPLC (Vydac; C18; diameter=4.6 mm; length=150 mm; gradient=$H_2O$ [0.1% $H_3PO_4$]—$CH_3CN$, 95%–5%, 5%–95%, over 16 minutes, 2 ml/min flow rate) RT=9.56 min; focus=215 nm; 99% pure.

Anal. Calcd for $C_{29}H_{27}F_4N_3O_2 \cdot 1.00$ HCl: C=61.97, H=5.02, N=7.48. Found: C=61.94, H=5.19, N=7.40.

EXAMPLE 36

Bis-3,4-difluorophenylacetic acid (32)

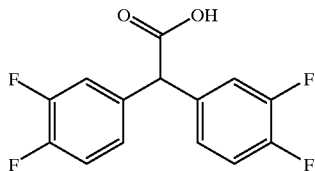

A solution of 2-trimethylsilyl-1,3-dithiane (2.43 g, 12.6 mmol) in tetrahydrofuran (50 mL) was cooled to −78° C. and treated with n-butyllithium (5.10 mL of 2.5 M). The reaction was stirred at −78° C. (10 min) and treated with a solution of 28 (3.06 g, 12.0 mmol) in tetrahydrofuran (25 mL) over 10 min. The resulting mixture was treated with 6 N HCl (50 mL) and warmed to room temperature. The reaction was stirred at room temperature (4 d). The solvent was removed in vacuo and the residue dissolved in methanol (40 mL) and 3 M KOH solution (16 mL) at room temperature (3 h). The solvent was removed in vacuo and the residue was dissolved in ethyl ether and aqueous KOH solution. The aqueous layer was extracted with two additional portions of ethyl ether and the combined organic extracts were discarded. The aqueous layer was acidified with 12 M HCl and extracted with three portions of ethyl ether. The combined organic extracts were washed with brine, dried over $Na_2SO_4$, and concentrated under reduced pressure to afford the title compound 32.

$^1$H NMR (CDCl$_3$, 400 MHz) consistant with assigned structure.

EXAMPLE 37

33

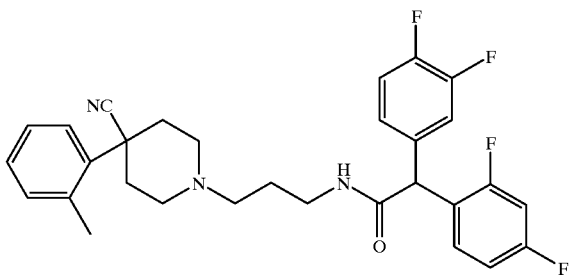

A solution of 32 (224 mg, 0.788 mmol), 26 (284 mg, 1.10 mmol), EDCI (166 mg, 0.866 mmol), and HOBT (117 mg, 0.866 mmol) in DMF (2 mL) was treated with diisopropylethylamine (300 μL, 1.722 mmol) at room temperature. The resulting mixture was stirred at room temperature overnight. The solvent was removed in vacuo. The residue was dissolved in dichloromethane and sodium bicarbonate solution. The aqueous layer was extracted with two additional portions of dichloromethane and the combined organic extracts were washed with brine, dried over $Na_2SO_4$, and concentrated under reduced pressure. PCTLC (SiO$_2$, 4mm, 5% EtOH; 95% CHCl$_3$) afforded 33 as the hydrochloride salt after treatment with methanolic HCl.

$^1$H NMR (CDCl$_3$, 400 MHz) consistant with assigned structure.

FABLRMS m/e 524 g/mole (M$^+$+H, C$_{30}$H$_{29}$F$_4$N$_3$O=524 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) RT=10.35 min; focus=215 nm; 97% pure.

Anal. Calcd for C$_{30}$H$_{29}$F$_4$N$_3$O.1.30 HCl.0.20 H$_2$O: C=62.71, H=5.39, N=7.31. Found: C=62.65, H=5.38, N=7.52.

EXAMPLE 38

34

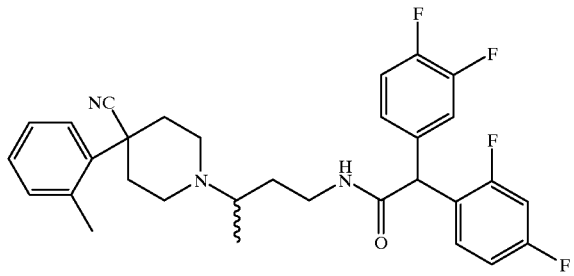

A solution of 32 (104 mg, 0.366 mmol), N-(2-(4-aminobutyl))-4-cyano-4-(o-tolyl)piperidine (89 mg, 0.328 mmol), EDCI (69 mg, 0.360 mmol), and HOBT (49 mg, 0.362 mmol) in DMF (1 mL) was treated with diisopropylethylamine (125 μL, 0.717 mmol) at room temperature. The resulting mixture was stirred at room temperature overnight. The solvent was removed in vacuo. The residue was dissolved in dichloromethane and sodium bicarbonate solution. The aqueous layer was extracted with two additional portions of dichloromethane and the combined organic extracts were washed with brine, dried over $Na_2SO_4$, and concentrated under reduced pressure. PCTLC (SiO$_2$, 4mm, 5% EtOH; 95% CHCl$_3$) afforded 34 as the hydrochloride salt after treatment with methanolic HCl.

$^1$H NMR (CDCl$_3$, 400 MHz) consistant with assigned structure.

FABLRMS m/e 538 g/mole (M$^+$+H, C$_{31}$H$_{31}$F$_4$N$_3$O=538 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) RT=10.63 min; focus=215 nm; 97% pure.

Anal. Calcd for C$_{31}$H$_{31}$F$_4$N$_3$O.1.65 HCl.0.65 DMF: C=61.33, H=5.81, N=7.92. Found: C=61.36, H=6.01, N=7.8.

EXAMPLE 39

35

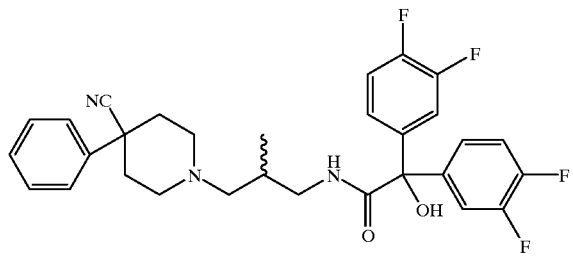

A solution of 30 (407 mg, 1.355 mmol), N-(3-amino-2-methylpropyl)-4-cyano-4-phenylpiperidine (348 mg, 1.352 mmol), EDCI (285 mg, 1.486 mmol), and HOBT (203 mg, 1.502 mmol) in DMF (1 mL) was treated with diisopropylethylamine (750 μL, 4.300 mmol) at room temperature. The resulting mixture was stirred at room temperature (2 d). The solvent was removed in vacuo. The residue was dissolved in dichloromethane and sodium bicarbonate solution. The aqueous layer was extracted with two additional portions of dichloromethane and the combined organic extracts were washed with brine, dried over $Na_2SO_4$, and concentrated under reduced pressure.

PCTLC ($SiO_2$, 4mm, 5% EtOH; 95% $CHCl_3$) afforded 35 as the hydrochloride salt after treatment with methanolic HCl.

$^1$H NMR ($CDCl_3$, 400 MHz) consistant with assigned structure.

FABLRMS m/e 540 g/mole ($M^+$+H, $C_{30}H_{29}F_4N_3O_2$=540 g/mole.)

HPLC (Vydac; C18; diameter=4.6 mm; length=150 mm; gradient=$H_2O$ [0.1% $H_3PO_4$]—$CH_3CN$, 95%-5%, 5%-95%, over 16 minutes, 2 ml/min flow rate) RT=10.13 min; focus=215 nm; 94% pure.

Anal. Calcd for $C_{30}H_{29}F_4N_3O_2$.0.95 HCl: C=62.75, H=5.26, N=7.32. Found: C=62.73, H=5.54, N=7.28.

EXAMPLE 40

36

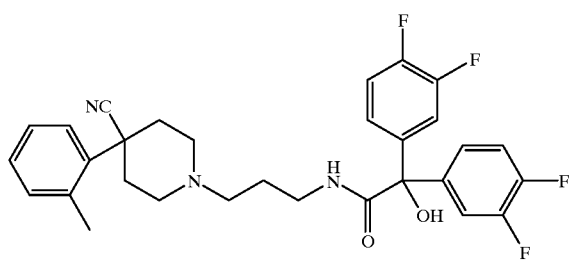

A solution of 30 (109 mg, 0.363 mmol), 26 (108 mg, 0.419 mmol), EDCI (80 mg, 0.417 mmol), and HOBT (58 mg, 0.429 mmol) in DMF (2 mL) was treated with diisopropylethylamine (408 μL, 2.34 mmol) at room temperature. The resulting mixture was stirred at room temperature (2 d). The solvent was removed in vacuo. The residue was dissolved in dichloromethane and sodium bicarbonate solution. The aqueous layer was extracted with two additional portions of dichloromethane and the combined organic extracts were washed with brine, dried over $Na_2SO_4$, and concentrated under reduced pressure. PCTLC ($SiO_2$, 4 mm, 5% EtOH; 95% $CHCl_3$) afforded 36 as the hydrochloride salt after treatment with methanolic HCl.

$^1$H NMR ($CDCl_3$, 400 MHz) consistant with assigned structure.

FABLRMS m/e 540 g/mole ($M^+$+H, $C_{30}H_{29}F_4N_3O_2$=540 g/mole.)

HPLC (Vydac; C18; diameter=4.6 mm; length=150 mm; gradient=$H_2O$ [0.1% $H_3PO_4$]—$CH_3CN$, 95%-5%, 5%-95%, over 16 minutes, 2 ml/min flow rate) RT=9.77 min; focus=215 nm; 97% pure.

Anal. Calcd for $C_{30}H_{29}F_4N_3O_2$.1.25 HCl.0.10 $H_2O$: C=61.38, H=5.23, N=7.16. Found: C=61.36, H=5.24, N=6.98.

EXAMPLE 41

Preparation of 1-Isopropyl-1-phenyl acetic acid analogs[1]

A 1.0 mole solution of a substituted phenyl acetic acid and dried THF under argon was chilled to −78° C. The solution was treated with 1 equivalent of a $LiN(TMS)_2$ (1 molar solution in THF). After 30 minutes, 1 equivalent of TMSCl (1 molar solution in THF) was added to the chilled solution followed by 2.2 equivalents of the $LiN(TMS)_2$. After 20 minutes, 10 equivalents of HMPA was added, followed by 30 equivalents of iodopropane.

The resulting mixture was stirred at −78° C. (1 h) and quenched by the addition of aqueous 5% HCl. The aqueous phase was extracted with EtOAc and the organic extract was washed twice with water and once with saturated aqueous NaCl, dried ($Na_2SO_4$), and concentrated in vacuo. Chromatography (PCTLC, $SiO_2$, 10–50% EtOAc-hexane) afforded the alkylated product 37, which was concentrated in vacuo.

37

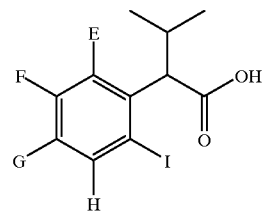

| # | E | F | G | H | I | HPLC[2] R.T. | NMR |
|---|---|---|---|---|---|---|---|
| 37a | H | —O—$CH_2$—O— | | H | H | 7.52 min. | ($CDCl_3$, 400 MHz) d = 6.74(d, 1H, J = 1 Hz), 6.75 (d, 2H, J = 2 Hz), 5.94(t, 2H, J = 2 Hz), 3.06(d, 1H, J = 11.6 Hz)2.76(m, 1H), 1.06(d, 3H, J = 6.4 Hz), 0.73(d, 3H, J = 6.4 Hz). |

| # | E | F | G | H | I | HPLC R.T. | NMR |
|---|---|---|---|---|---|---|---|
| 37b | H | F | F | H | H | 9.12 min. | ($CDCl_3$, 400 MHz) d = 7.22(m, 1H), 7.19(m, 2H), 3.13(d, 1H, J = 10.4 Hz) |

-continued

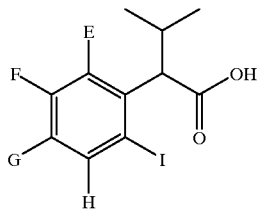

37

| | E | F | G | H | I | | |
|---|---|---|---|---|---|---|---|
| 37c | H | F | F | F | H | 10.08 min. | 2.62(m, 1H), 1.07(d, 3H, J = 6.4 Hz), 0.74(d, 3H, 6.4 Hz) (CDCl$_3$, 400 MHz) d = 7.99(dd, 2H, J = 6.4 Hz), 3.08(d, 1H, J = 10.4 Hz), 2.22(m, 1H), 1.06(d, 3H, J = 6.4 Hz), 0.88(d, 3H, J = 6.4 Hz). |
| 37d | H | F | H | F | H | 9.25 min. | (CDCl$_3$, 400 MHz) d = 6.90(m, 2H), 6.73(m, 1H), 3.14(d, 1H, J = 10.4 Hz), 2.27 (m, 1H), 1.19(d, 3H, J = 6.4 Hz), 0.76(d, 3H, J = 6.4 Hz). |
| 37e | H | CH$_3$ | CH$_3$ | H | H | 11.17 min. | (CDCl$_3$, 400 MHz) d = 7.06(m, 3H), 3.09(d, 1H, J = 10.6 Hz), 2.31(m, 1H), 2.23(d, 6H, J = 5.1 Hz), 1.07(d, 3H, J = 6.6 Hz), 0.71(d, 3H, J = 6.6 Hz). |
| 37f | H | OMe | OMe | H | H | 9.14 min. | (CDCl$_3$, 400 MHz) d = 6.87(s, 2H), 6.45(d, 1H, J = 2.0 Hz), 6.79(s, 1H), 3.07(d, 1H, J = 10.6 Hz), 2.28(m, 1H), 1.07(d, 3H, J = 6.6 Hz), 0.72 (d, 3H, J = 6.6 Hz). |
| 37g | H | F | H | H | H | — | (CDCl$_3$, 400 MHz) d = 7.28(m, 1H), 7.08(m, 2H), 6.97(m, 1H), 3.16(d, 1H, J = 6.5 Hz), 2.26(m, 1H), 1.08(d, 3H, J = 6.6 Hz), 0.73(d, 3H, J = 6.6 Hz). |

[2]Vydac; C18; diameter = 4.6 mm; length = 15 cm; gradient = CH$_3$CN [0.1% TFA ]- H$_2$O [0.1% TFA], 5%–95%, 95%–5% over 20 min. 1.5 ml/min flow rate; focus = 215 nm

EXAMPLE 42

Preparation of 1-Arylcyclopropanecarbonitrile Analogs[3]

[3] Fedorynski, Michal; Jonczyk, Andrzej. *Organic Preperation and Procedures Int.,* 1995, 27,335.

To a stirred mixture with 1 equivalent of the nitrile, 0.02 equivalents of the TEBAC and 2 equivalents of BCE, 50% aq. NaOH was added dropwise at 45° C. After addition, the reaction continued at 45° C. for 18 hours.

The reaction mixture was diluted with water, the organic products were extracted with EtOAc. The organic extract was washed twice with water and once with saturated aqueous NaCl, dried (Na$_2$SO$_4$), and concentrated in vacuo. Chromatography (PCTLC, SiO$_2$, 10–50% EtOAc-hexane) afforded the alkylated product 38, which was concentrated in vacuo.

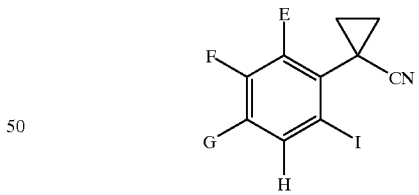

38

| # | E | F | G | H | I | NMR |
|---|---|---|---|---|---|---|
| 38a | H | CH$_3$ | CH$_3$ | H | H | (CDCl$_3$, 400 MHz) d = 7.06(m, 3H), 2.27(s, 3H), 2.25(s, 3H), 1.68 (m, 2H), 1.36(m, 2H). |
| 38b | H | F | F | H | H | (CDCl$_3$, 400 MHz) d = 7.11(m, 3H), 1.73(m, 2H), 1.36(m, 2H). |

EXAMPLE 43

Preparation of 1-Phenyl-1-cyclopropanecarbon acetic acid analogs

A large excess of 15 M HCl was added to the nitrile. The reaction mixture was heated to 100° C. The resulting mixtured was stirred at 100° C. for 18 hours. EtOAc was added to extract the organic product. The organic extract was washed twice with water and once with concentrated NaCl, dried (Na$_2$SO$_4$), and concentrated in vacuo. Chromatography (PCTLC, SiO$_2$, 10–50% EtOAc-hexane) afforded the hydrolized product, which was concentrated in vacuo.

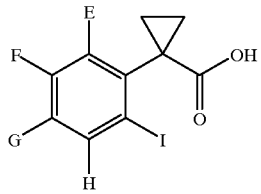

39

| # | E | F | G | H | I | HPLC R.T. | NMR |
|---|---|---|---|---|---|---|---|
| 39a | H | CH$_3$ | CH$_3$ | H | H | 8.97 min. | (CDCl$_3$, 400 MHz) d = 7.28 (br-s, 1H), 7.54(br-s, 1H), 7.10(br-s, 1H), 2.27(s, 3H), 2.10(s, 3H), 1.66(m, 2H), 1.24(m, 2H). |
| 39b | H | F | F | H | H | 8.33 min. | (CDCl$_3$, 400 MHz) d = 7.13 (m, 3H), 1.70(m, 2H), 1.26 (m, 2H). |

EXAMPLE 44

Preparation of Phenylpiperidin-1-yl propyl-2-phenyl acetamide analogs

A solution of the phenyl-N-(3-amino)propyl piperidine dihydrochloride (1 equivalent) and the phenyl acetic acid (1 equivalent) in DMF (0.50 M) was treated with 1-(3-dimethyl-aminopropyl)-3-ethylcarbodimide hydrochloride (EDCI), (1.5 equivalent), 1-hydroxybenzotriazole hydrate (HOBt), (1.5 equivalents), and NaHCO$_3$ (5.0 equivalents) at room temperature (18 h). The solvent was removed in vacuo, the residue was dissolved in EtOAc and washed with saturated NaHCO$_3$, H$_2$O (2×) and saturated aqueous NaCl, dried (Na$_2$SO$_4$) and concentrated in vacuo. PCTLC (SiO$_2$, 4 mm, 1:1 hexane: EtOAc) afforded the product 40.

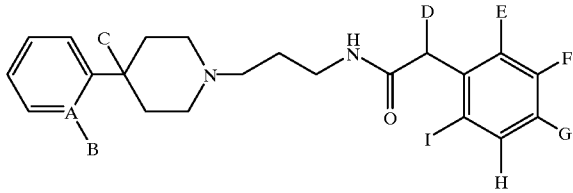

40

| # | A | B | C | D | E | F | G | H | I | FABLRMS[4] | HPLC[5] R.T. | Elemental Analysis |
|---|---|---|---|---|---|---|---|---|---|---|---|---|
| 40a | C | OCH$_3$ | CN | tolyl | H | H | CH$_3$ | H | H | M + 1 = 496 g/mole C$_{32}$H$_{37}$N$_3$O$_2$ = 495.7 g/mole | 10.28 min. | Calc. for 0.35 H$_2$O Solvate mol. wt. = 501.97 g/mole Calc.: C = 54.57% H = 5.63% N = 7.82% Found: C = 54.53% H = 5.55% N = 7.83% |
| 40b | N | — | CN | tolyl | H | H | CH$_3$ | H | H | M + 1 = 467 g/mole C$_{30}$H$_{34}$N$_4$O$_1$ = 466.63 g/mole | 9.14 min. | Calc. for 0.20 H$_2$O Solvate mol. wt. = 471.13 g/mole Calc.: C = 76.48% H = 7.32% N = 12.01% Found: C = 76.45% H = 7.27% N = 11.79% |
| 40c | C | CF$_3$ | CN | tolyl | H | H | CH$_3$ | H | H | M + 1 = 534 g/mole C$_{32}$H$_{34}$N$_3$OF$_3$ = 533.64 g/mole | 10.84 min. | Calc. for 0.95 H$_2$O, 0.05 CH$_2$Cl$_2$ Solvate mol. wt. = 555.00 g/mole Calc.: C = 69.36% H = 6.54% N = 7.57% Found: C = 69.36% H = 6.52% N = 7.24% |

-continued

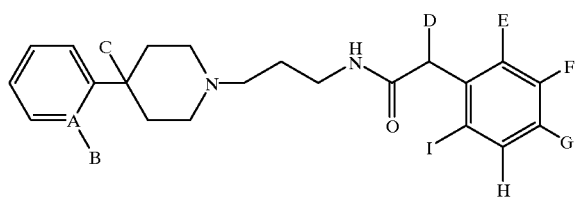

40

| # | A | B | C | D | E | F | G | H | I | FABLRMS[4] | HPLC[5] R.T. | Elemental Analysis |
|---|---|---|---|---|---|---|---|---|---|---|---|---|
| 40d | C | H | CN | phenyl | H | H | H | H | H | M + 1 = 438 g/mole $C_{29}H_{31}N_3O$ = 437.5 g/mole | 9.06 min. | Calc. for 0.15 $H_2O$ Solvate mol. wt. = 437.59 g/mole Calc.: C = 79.11% H = 7.17% N = 9.54% Found: C = 79.05% H = 7.12% N = 9.46% |
| 40e(+) | C | H | CN | cyclo-hexyl | H | H | H | H | H | M + 1 = 444 g/mole $C_{29}H_{37}N_3O$ = 443.64 g/mole | 10.19 min. | Calc. for 0.65 $H_2O$ Solvate mol. wt. = 455.35 g/mole Calc.: C = 76.50% H = 8.48% N = 9.23% Found: C = 76.52% H = 8.41% N = 9.47% |
| 40f(+)[6] | C | H | CN | cyclo-hexyl | H | H | H | H | H | M + 1 = 444 g/mole $C_{29}H_{37}N_3O$ = 443.64 g/mole | 10.19 min. | Calc. for 0.75 $H_2O$ Solvate mol. wt. = 457.14 g/mole Calc.: C = 76.20% H = 8.49% N = 9.19% Found: C = 76.25% H = 8.17% N = 9.11% |
| 40g(−)[6] | C | H | CN | cyclo-hexyl | H | H | H | H | H | M + 1 = 444 g/mole $C_{29}H_{37}N_3O$ = 443.64 g/mole | 10.19 min. | Calc. for 0.60 $H_2O$ Solvate mol. wt. = 454.45 g/mole Calc.: C = 76.65% H = 8.47% N = 9.25% Found: C = 76.59% H = 8.20% N = 9.31% |
| 40h(+) | C | H | CN | cyclo-pentyl | H | H | H | H | H | M + 1 = 430 g/mole $C_{28}H_{35}N_3O$ = 429.60 g/mole | 9.19 min. | Calc. for 0.25 $H_2O$ Solvate mol. wt. = 434.11 g/mole Calc.: C = 77.47% H = 8.24% N = 9.68% Found: C = 77.45% H = 8.08% N = 9.88% |
| 40i(−)[7] | C | H | CN | cyclo-pentyl | H | H | H | H | H | M + 1 = 430 g/mole $C_{28}H_{35}N_3O$ = 429.60 g/mole | 9.19 min. | Calc. for 0.20 $H_2O$, 0.40 $CH_2Cl_2$ Solvate mol. wt. = 468.26 g/mole Calc.: C = 73.02% H = 7.81% N = 8.99% Found: C = 73.01% H = 7.62% N = 9.18% |
| 40j(+)[7] | C | H | CN | cyclo-pentyl | H | H | H | H | H | M + 1 = 430 g/mole $C_{28}H_{35}N_3O$ = 429.60 g/mole | 9.19 min. | Calc. for 0.65 $H_2O$ Solvate mol. wt. = 468.26 g/mole Calc.: C = 76.21% H = 8.29% N = 9.52% Found: C = 76.19% H = 7.94% N = 9.42% |
| 40k(+) | C | H | CN | iso-propyl | H | H | H | H | H | M + 1 = 404 g/mole $C_{26}H_{33}N_3O$ = 403.57 g/mole | 8.93 min. | Calc.: C = 77.38% H = 8.24% N = 10.41% Found: C = 77.07% H = 8.14% N = 10.42% |
| 40l(−)[8] | C | H | CN | iso-propyl | H | H | H | H | H | M + 1 = 404 g/mole $C_{26}H_{33}N_3O$ = 403.57 g/mole | 8.93 min. | Calc. for 0.35 $H_2O$, 0.15 $CHCl_3$ Solvate mol. wt. = 427.78 g/mole Calc.: C = 73.42% H = 7.98% N = 9.82% Found: C = 73.35% H = 7.94% N = 10.07% |
| 40m(+)[8] | C | H | CN | iso-propyl | H | H | H | H | H | M + 1 = 404 g/mole $C_{26}H_{33}N_3O$ = | 8.93 min. | Calc. for 0.60 $H_2O$ Solvate mol. |

-continued

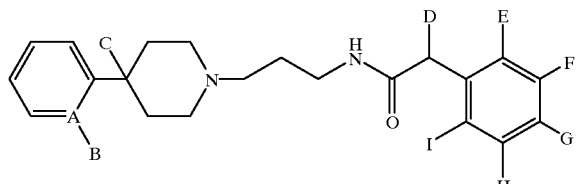

40

| # | A | B | C | D | E | F | G | H | I | FABLRMS[4] | HPLC[5] R.T. | Elemental Analysis |
|---|---|---|---|---|---|---|---|---|---|---|---|---|
| | | | | | | | | | | 403.57 g/mole | | wt. = 414.38 g/mole<br>Calc.: C = 75.36%<br>H = 8.32% N = 10.14%<br>Found: C = 75.33%<br>H = 7.93% N = 10.27% |
| 40n(+)[9] | C | $CH_3$ | CN | iso-propyl | H | F | F | H | H | M + 1 = 454 g/mole<br>$C_{27}H_{33}N_3OF_2 \cdot HCl$ =<br>490.04 g/mole | 9.65 min. | Calc. for 0.10 $H_2O$,<br>0.25 $CHCl_3$<br>Solvate mol.<br>wt. = 521.69 g/mole<br>Calc.: C = 62.74%<br>H = 6.66% N = 8.05%<br>Found: C = 62.73%<br>H = 6.81% N = 8.09% |
| 40o(−)[10] | C | $CH_3$ | CN | iso-propyl | H | F | F | H | H | M + 1 = 454 g/mole<br>$C_{27}H_{33}N_3OF_2$ =<br>454.58 g/mole | 9.65 min. | Calc. for 0.80 $H_2O$,<br>0.50 EtOAc<br>Solvate mol.<br>wt. = 511.42 g/mole<br>Calc.: C = 68.03%<br>H = 7.60% N = 8.21%<br>Found: C = 68.11%<br>H = 7.26% N = 8.19% |
| 40p(+)[9,10] | C | $CH_3$ | CN | iso-propyl | H | F | F | H | H | M + 1 = 454 g/mole<br>$C_{27}H_{33}N_3OF_2 \cdot HCl$ =<br>490.04 g/mole | 9.65 min. | Calc. for 1.90 $H_2O$,<br>0.90 $CHCl_3$<br>Solvate mol.<br>wt. = 631.70 g/mole<br>Calc.: C = 53.05%<br>H = 6.18% N = 6.65%<br>Found: C = 53.02%<br>H = 6.13% N = 6.78% |
| 40q(+) | N | — | CN | iso-propyl | H | F | F | H | H | M + 1 = 441 g/mole<br>$C_{25}H_{30}N_4OF_2$ =<br>440.54 g/mole | 8.59 min. | Calc. for 0.40 $H_2O$<br>Solvate mol.<br>wt. = 447.74 g/mole<br>Calc.: C = 67.06%<br>H = 6.93% N = 12.51%<br>Found: C = 67.02%<br>H = 6.76% N = 12.35% |
| 40r(+)[9] | C | OMe | CN | iso-propyl | H | F | F | H | H | M + 1 = 470 g/mole<br>$C_{27}H_{33}N_3O_2F_2 \cdot HCl$ =<br>506.04 g/mole | 9.60 min. | Calc. for 0.35 $H_2O$<br>Solvate mol.<br>wt. = 536.22 g/mole<br>Calc.: C = 60.93%<br>H = 6.56% N = 7.84%<br>Found: C = 60.91%<br>H = 6.59% N = 7.96% |
| 40s(+)[9] | C | $CH_3$ | CN | iso-propyl | F | H | F | H | H | M + 1 = 454 g/mole<br>$C_{27}H_{33}N_3OF_2 \cdot HCl$ =<br>490.04 g/mole | 9.14 min. | Calc. for 0.85 $H_2O$<br>Solvate mol.<br>wt. = 505.35 g/mole<br>Calc.: C = 64.17%<br>H = 7.12% N = 8.32%<br>Found.: C = 64.17%<br>H = 6.81% N = 8.20% |
| 40t(+)[9] | C | $CH_3$ | CN | iso-propyl | H | F | H | F | H | M + I = 454 g/mole<br>$C_{27}H_{33}N_3OF_2 \cdot HCl$ =<br>490.04 g/mole | 9.31 min. | Calc. for 0.80 EtOAc<br>Solvate mol.<br>wt. = 560.52 g/mole<br>Calc.: C = 64.77%<br>H = 7.08% N = 7.27%<br>Found: C = 64.7 1%<br>H = 7.26% N = 7.27% |
| 40u(+)[9] | C | $CH_3$ | CN | iso-propyl | H | H | H | H | H | M + I = 436 g/mole<br>$C_{27}H_{34}N_3OF \cdot HCl$ =<br>472.05 g/mole | 9.04 min. | Calc. for 0.30 EtOAc<br>Solvate mol.<br>wt. = 498.48 g/mole<br>Calc.: C = 67.95%<br>H = 7.56% N = 8.43%<br>Found: C = 67.97%<br>H = 7.65% N = 8.34% |

-continued

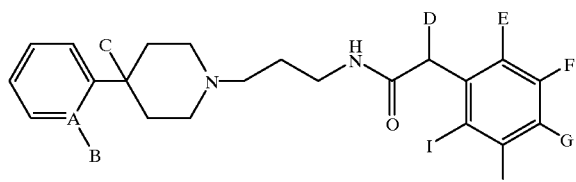

40

| # | A | B | C | D | E | F | G | H | I | FABLRMS[4] | HPLC[5] R.T. | Elemental Analysis |
|---|---|---|---|---|---|---|---|---|---|---|---|---|
| 40v(+)[9] | C | $CH_3$ | CN | iso-propyl | H | H | F | H | H | M + 1 = 436 g/mole $C_{27}H_{34}N_3OF.HCl$ = 472.05 g/mole | 9.43 min. | Calc. for 0.95 $H_2O$, 0.20 EtOAc Solvate mol. wt. = 506.18 g/mole Calc.: C = 65.89% H = 7.66% N = 8.29% Found: C = 65.87% H = 7.35% N = 8.32% |
| 40w(+)[9] | C | $CH_3$ | CN | iso-propyl | H | F | F | F | H | M + 1 = 472 g/mole $C_{27}H_{32}N_3OF_3.HCl$ = 508.03 g/mole | 9.87 min. | Calc. for 0.20 $H_2O$, 0.65 $CHCl_3$ Solvate mol. wt. = 589.23 g/mole Calc.: C = 56.36% H = 5.82% N = 7.13% Found: C = 56.31% H = 5.86% N = 7.14% |
| 40x(−)[11] | C | $CH_3$ | CN | iso-propyl | H | F | F | F | H | M + 1 = 472 g/mole $C_{27}H_{32}N_3OF_3$ = 471.47 g/mole | 9.87 min. | |
| 40y(+)[11] | C | $CH_3$ | CN | iso-propyl | H | F | F | F | H | M + 1 = 472 g/mole $C_{27}H_{32}N_3OF_3$ = 471.47 g/mole | 9.87 min. | |
| 40z(+)[9] | C | $CH_3$ | CN | iso-propyl | H | H | $CF_3$ | H | H | M + 1 = 486 g/mole $C_{28}H_{34}N_3OF_3.HCl$ = 521.24 g/mole | 10.36 min. | Calc. for 0.80 $H_2O$, 0.95 $CH_2Cl_2$ Solvate mol. wt. = 617.15 g/mole Calc.: C = 56.34% H = 6.13% N = 6.81% Found.: C = 56.34% H = 6.18% N = 6.97% |
| 40aa(+)[9] | C | $CH_3$ | CN | iso-propyl | H | H | Cl | H | H | M + 1 = 452 g/mole $C_{27}H_{33}N_3OCl.2HCl$ = 523.96 g/mole | 9.92 min. | Calc. for 0.05 $H_2O$, 0.55 $CHCl_3$ Solvate mol. wt. = 581.53 g/mole Calc.: C = 55.94% H = 6.25% N = 7.10% Found: C = 55.93% H = 6.31% N = 6.91% |
| 40bb(+)[9] | C | $CH_3$ | CN | iso-propyl | H | OMe | OMe | H | H | M + 1 = 478 g/mole $C_{29}H_{39}N_3O_3.HCl$ = 514.31 g/mole | 8.58 min. | Calc. for 1.0 hexane, 1.0 EtOAc Solvate mol. wt. = 686.39 g/mole Calc.: C = 68.25% H = 8.81% N = 6.12% Found: C = 68.18% H = 8.66% N = 6.15% |
| 40cc(+)[9] | C | $CH_3$ | CN | iso-propyl | H | Me | Me | H | H | M + 1 = 446 g/mole $C_{29}H_{39}N_3O.HCl$ = 482.12 g/mole | 10.01 min. | Calc. for 0.20 $H_2O$, 0.90 EtOH Solvate mol. wt. = 527.18 g/mole Calc.: C = 70.17% Found: C = 70.17% H = 8.78% N = 7.60% |
| 40dd(+)[9] | C | $CH_3$ | CN | iso-propyl | H | —$OCH_2O$— | | H | H | M + 1 = 462 g/mole $C_{28}H_{35}N_3O_3.HCl$ = 498.08 g/mole | 8.85 min. | Calc. for 0.55 $H_2O$, 0.20 $CHCl_3$ Solvate mol. wt. = 531.85 g/mole Calc.: C = 63.52% H = 7.29% N = 8.44% Found: C = 63.7 1% H = 7.07% N = 7.89% |
| 40ee(+)[9] | C | $CH_3$ | CN | H | H | F | F | F | H | M + 1 = 430 g/mole $C_{27}H_{26}N_3OF_3.HCl$ = | 8.41 min. | Calc. for 1.0 hexane, |

-continued

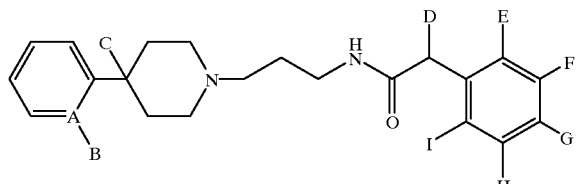

40

| # | A | B | C | D | E | F | G | H | I | FABLRMS[4] | HPLC[5] R.T. | Elemental Analysis |
|---|---|---|---|---|---|---|---|---|---|---|---|---|
| | | | | | | | | | | 465.91 g/mole | | 0.60 H$_2$O Solvate mol. wt. = 465.95 g/mole Calc.: C = 64.01% H = 7.56% N = 7.46% Found: C = 64.01% H = 6.93% N = 6.46% |
| 40ff[9] | C | CH$_3$ | CN | —CH$_2$CH$_2$— | H | CH$_3$ | CH$_3$ | H | H | M + 1 = 430 g/mole C$_{28}$H$_{35}$N$_3$O.HCl = 466.07 g/mole | 9.18 min. | Calc. for 0.75 H$_2$O Solvate mol. wt. = 479.58 g/mole Calc.: C = 70.13% H = 7.88% N = 8.76% Found: C = 70.17% H = 7.82% N = 8.68% |
| 40gg[9] | C | CH$_3$ | CN | —CH$_2$CH$_2$— | H | F | F | H | H | M + 1 = 438 g/mole C$_{26}$H$_{29}$N$_3$OF$_2$.HCl = 474.00 g/mole | 9.03 min. | Calc. for 0.75 H$_2$O Solvate mol. wt. = 487.51 g/mole Calc.: C = 64.06% H = 6.51% N = 8.63% Found: C = 64.05% H = 6.45% N = 8.35% |
| 40hh[9] | N | — | H | iso-propyl | H | F | F | H | H | M + 1 = 488.45 g/mole C$_{24}$H$_{31}$N$_3$OF$_2$.2HCl =Solvate mol. 488.45 g/mole Calc.: C = 52.06% | 6.95 min. | H = 6.31% N = 7.43% Found: C = 52.08% H = 6.57% N = 7.50% wt. = 565.25 g/mole |
| 40ii | C | CH$_3$ | CN | iso-propyl | H | H | CH$_3$ | H | H | | 9.66 min. | Calc. for 0.85 H$_2$O Solvate mol. wt. = 483.4 g/mole Calc.: C = 69.57% H = 8.28% N = 8.69% Found: C = 69.52% H = 8.04% N = 8.92% |
| 40jj[9] | N | — | H | p-tolyl | H | H | CH$_3$ | H | H | | 7.54 min. | |
| 40kk[9] | C | CH$_3$ | CN | N(Me)$_2$ | H | H | F | H | H | | 6.67 min. | Calc. for 1.6 H$_2$O and 0.85 C$_6$H$_6$ Solvate mol. wt. = 641.182 g/mole Calc.: C = 58.25% H = 6.96% N = 8.74% Found: C = 58.21% H = 6.57% N = 8.53% |
| 40ll[9] | C | H | H | iso-propyl | H | F | F | H | H | | 9.69 min. | Calc. for 1.0 HCl and 0.2 CHCl$_3$ Solvate mol. wt. = 451.00 g/mole Calc.: C = 63.74% H = 7.05% N = 5.90% Found: C = 63.45% H = 7.16% N = 6.03% |
| 40mm[9] | C | CH$_3$ | CN | cyclo-propyl | H | H | Cl | H | H | | 9.30 min. | Calc. for 1.15 H$_2$O and 1.0 HCl Solvate mol. wt. = 507.206 g/mole |

-continued

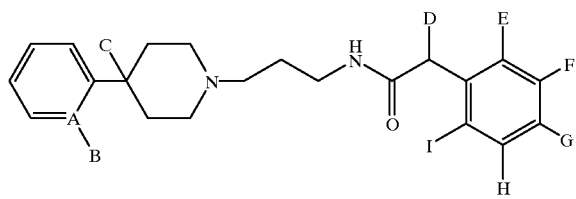

40

| # | A | B | C | D | E | F | G | H | I | FABLRMS[4] | HPLC[5] R.T. | Elemental Analysis |
|---|---|---|---|---|---|---|---|---|---|---|---|---|
| 40nn[9] | C | CH$_3$ | CN | cyclopropyl | H | F | F | H | H | | 9.18 min. | Calc.: C = 63.93% H = 7.02% N = 8.29% Found: C = 63.88% H = 7.07% N = 8.30% Calc. for 0.95 EtOAc and 1.0 HCl Solvate mol. wt. = 571.726/mole Calc.: C = 64.70% H = 6.98% N = 7.35% Found: C = 64.62% H = 6.90% N = 7.71% |

[4]3:1 mixture of dithiothreitol and dithioerthritol in MeOH.
[5]Vydac; C18; diameter = 4.6 mm; length = 15 cm; gradient = CH$_3$CN [0.1% TFA] - H$_2$O [0.1% TAF], 5% - 95%, 95% - 5% over 20 min. 1.5 ml/min. flow rate; focus = 215 nm.
[6]Separated by HPLC using a Welk-O (S,S) prep. column; diameter = 250 mm. length = 10 cm, isocratic 40% hexane [0.02% TFA], 40% n-butyl chloride [0.02% TFA], 20% EtOH [0.02% TFA]. 2.0 ml/min. flow rate; focus = 250 nm.
[7]Separated by HPLC using a Welk-O (S,S) prep. column; diameter = 250 mm, length = 10 cm, isocratic 35% hexane [0.20% TFA], 35% n-butyl chloride [0.20% TFA], 30% EtOH [0.20% TFA]. 2.0 ml/min. flow rate; focus = 250 nm.
[8]Separated by HPLC using a Welk-O (R,R) prep. column; diameter = 250 mm, length = 10 cm, isocratic 95% n-butyl chloride, 5% MeOH [0.02% HOAc, 0.02% NH$_4$OH]. 2.0 ml/min. flow rate; focus = 250 nm.
[9]The HCl salt was made by adding a solution of HCl-EtOAc (in excess) to the freebase. The resulting mixture was allowed to react for 1 hour at room temperature. The EtOAc was removed in vacuo affording the hydrochloride salt as a white solid.
[10]Separated by HPLC using a Welk-O (S,S) prep column; diameter = 250 mm, length = 10 cm, isocratic 50% hexane, 50% EtOH [0.02% HOAc, 0.02% NH$_4$OH], 2.0 ml/min. flow rate; focus = 225 nm and 212 nm.
[11]Separated by Chiracel O.D. prep. column; diameter = 250 mm, length = 10 cm, isocratic 85% hexane [0.1% TFA, 0.01% diethylamine], 15% EtOH [0.1% TFA, 0.01% diethylamine]. 4.0 ml/min. flow rate; focus = 250 nm.

In addition, Compounds 42 through 46 were made according to Schemes 3–5 and the description which follows.

SCHEME 3

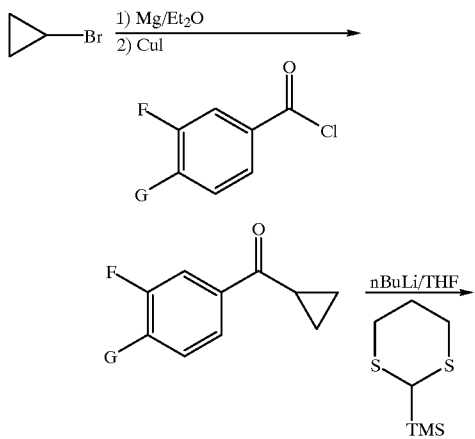

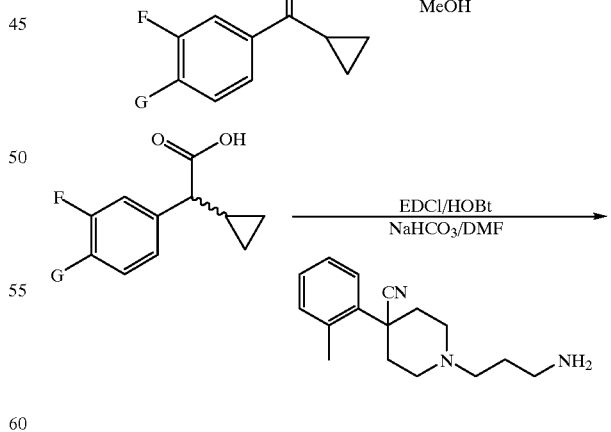

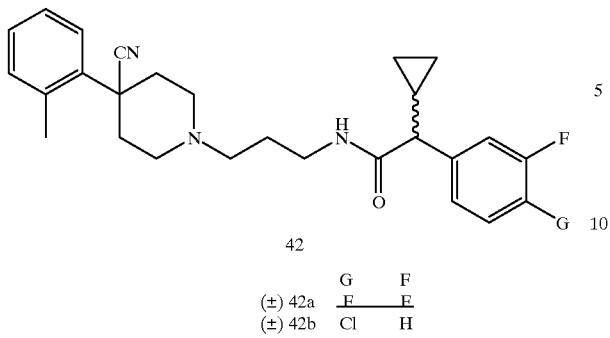

42

| | G | F |
|---|---|---|
| (±) 42a | F | F |
| (±) 42b | Cl | H |

The two required cyclopropylphenylacetic acids were prepared in three steps from commercially available starting materials.

First, reaction of the cyclopropyl cuprate, which was derived from the reaction of cyclopropyl magnesium bromide and copper (I) iodide, and a substituted benzoyl chloride provided the cyclopropylphenyl ketone in good yield, Modified Peterson olefination of the ketone with the carbanion generated from 2-trimethylsilyl 1,3-dithiane produced the bis thioketene acetal in excellent yield. These intermediates were hydrolyzed to the desired cyclopropylphenylacetic acids. The acids were coupled to a primary amine with EDCI/HOBt/NaHCO$_3$/DMF.

(±) 42b: $^1$H NMR consistent with chemical structure. HPLC Analysis Vydac; C18; diameter=4.6 mm; length=15 cm; gradient=CH$_3$CN [0.1% TFA]—H$_2$O 10.1% TFA], 5%–95%, 95%–5% over 20 min. 1.5 ml/min. flow rate; focus=215 nm, RT=9.30 min.

Analysis solvate MW 507.206 1.0 HCl & 1.15 H$_2$O

Calc C: 63.93% H: 7.02% N: 8.29%

Found C: 63.88% H: 7.07% N; 8.30%

(±) 42a: $^1$H NMR consistent with chemical structure. HPLC Analysis Vydac; C18; diameter=4.6 mm; length=15 cm; gradient=CH$_3$CN [0.1% TFA]—H$_2$O [0.1% TFA], 5%–95%, 95%–5% over 20 min. 1.5 ml/min. flow rate; focus=215 nm, RT=9.18 min.

Analysis solvate MW 571.727 1.0 HCl & 0.95 EtOAc

Calc C: 64.70% H: 6.98% N: 7.35%

Found C: 64.62% H: 6.90% N; 7.71%

SCHEME 4

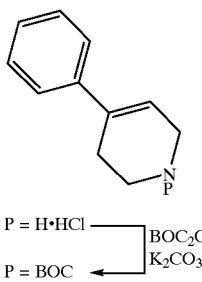

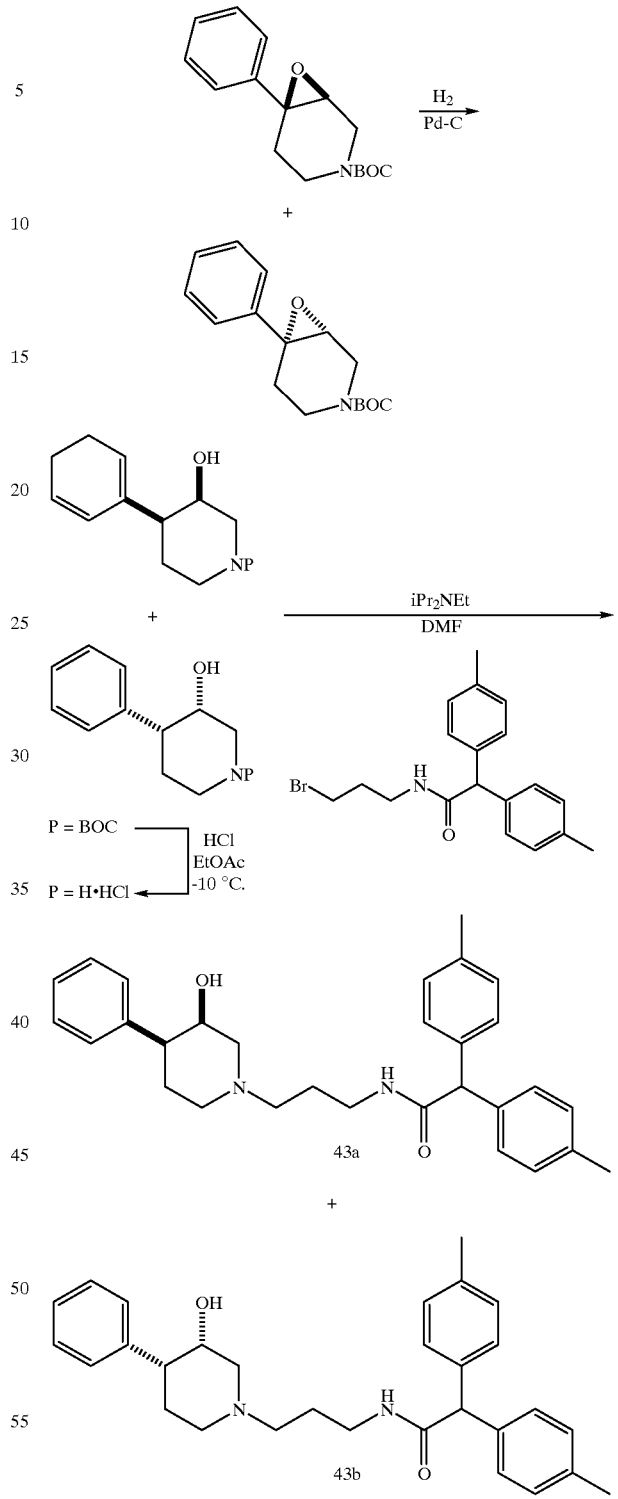

Oxidation of the NBOC protected 4-phenyl 1,2,3,6-tertrahydropyridine with mCPBA provided the racemic epoxide in excellent yield, Hydrogenation provided the (±) cis 3-hydroxy 4-phenyl piperidine, which was deprotected carefully with HCl/EtOAc at −10° C. The resulting amine was alkylated with the appropriate aliphatic bromide providing the desired tertiary amine.

(±) 43: ¹H NMR consistent with chemical structure. HPLC Analysis Vydac; C18; diameter=4.6 mm; length=15 cm; gradient=CH$_3$CN [0.1% TFA]—H$_2$O [0.1% TFA], 5%–95%, 95%–5% over 20 min. 1.5 ml/min. flow rate; focus=215 nm, RT=9.95 min.

Analysis solvate MW 486.476 0.26 CHCl$_3$.

Calc C: 64.70% H: 6.98% N: 7.35%

Found C: 64.62% H: 6.90% N; 7.71%

SCHEME 5

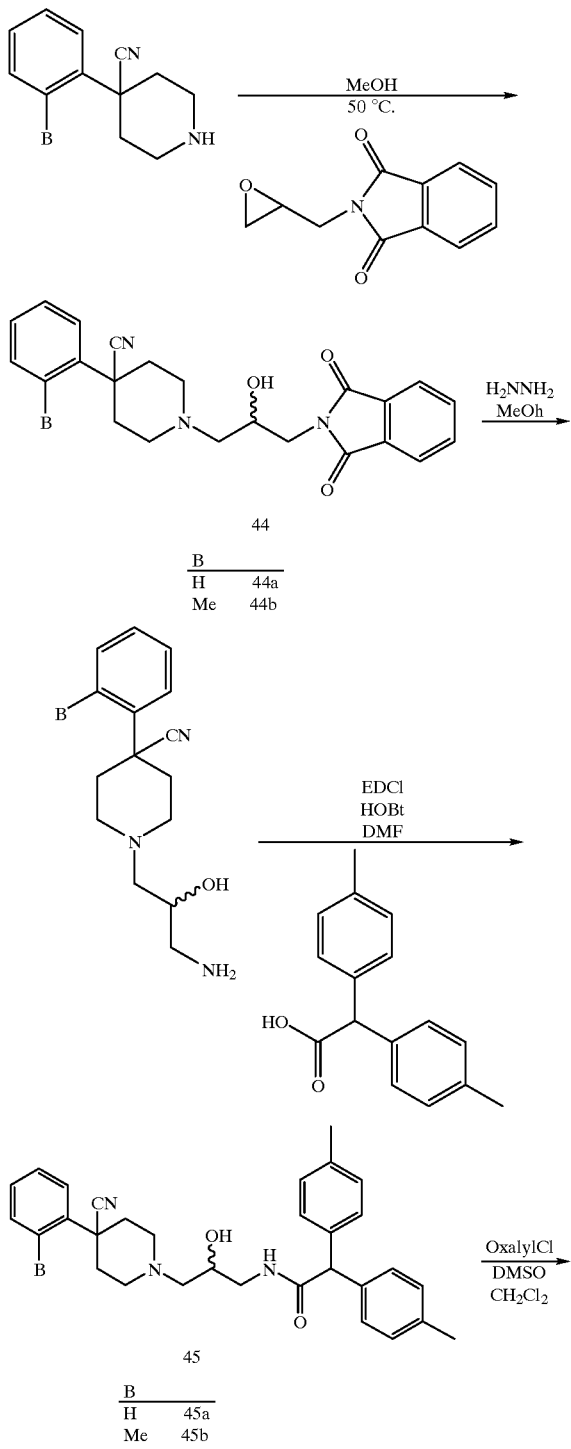

The reaction of 4-cyano 4-arylpiperidines with 2,3-epoxy-1-phthalimide provided the 2-hydroxy amines which were deprotected and acylated providing 45a and 45b. The hydroxyl groups were Swern oxidized to the corresponding ketones 46a and 46b.

(±) 44a: ¹H NMR consistent with chemical structure. HPLC Analysis Vydac; C18; diameter=4.6 mm; length=15 cm; gradient=CH$_3$CN [0.1% TFA]—H$_2$O [0.1% TFA], 5%–95%, 95%–5% over 20 min. 1.5 ml/min. flow rate; focus=215 nm, RT=7.12 min.

Analysis solvate MW 395.764 0.35 H$_2$O.

Calc C: 69.80% H: 6.04% N: 10.62%

Found C: 70.08% H: 6.04% N; 10.22%

(±) 44b: ¹H NMR consistent with chemical structure. HPLC Analysis Vydac; C18; diameter=4.6 mm; length=15 cm; gradient=CH$_3$CN [0.1% TFA]—H$_2$O [0.1% TFA], 5%–95%, 95%–5% over 20 min. 1.5 ml/min. flow rate; focus=215 nm, RT=7.51 min.

Analysis solvate MW 455.449 0.3 Et$_2$O & 0.35 CH$_2$Cl$_2$.

Calc C: 67.37% H: 6.35% N: 9.23%

Found C: 67.05% H: 5.97% N; 9.54%

(±) 45a: ¹H NMR consistent with chemical structure. HPLC Analysis Vydac; C18; diameter=4.6 mm; length=15 cm; gradient=CH$_3$CN [0.1% TFA]—H$_2$O [0.1% TFA], 5%–95%, 95%–5% over 20 min. 1.5 ml/min. flow rate; focus=215 nm, RT=9.71 min.

Analysis solvate MW 498.757 0.95 H$_2$O.

Calc C: 74.65% H: 7.46% N: 8.43%

Found C: 74.62% H: 7.07% N; 8.30%

(±) 45b: ¹H NMR consistent with chemical structure. HPLC Analysis Vydac; C18; diameter=4.6 mm; length=15 cm; gradient=CH$_3$CN [0.1% TFA]—H$_2$O [0.1% TFA], 5%–95%, 95%–5% over 20 min. 1.5 ml/min. flow rate; focus=215 nm, RT=10.15 min.

Analysis solvate MW 543.788 0.25 DMF & 0.25 CHCl$_3$.

Calc C: 72.88% H: 7.23% N: 8.37% Found C: 72.86% H: 7.11% N; 8.25%

(±) 46a: ¹H NMR consistent with chemical structure. HPLC Analysis Vydac; C18; diameter=4.6 mm; length=15 cm; gradient=CH$_3$CN [0.1% TFA]—H$_2$O [0.1% TFA], 5%–95%, 95%–5% over 20 min. 1.5 ml/min. flow rate; focus=215 nm, RT=10.13 min.

Analysis solvate MW 494.039 0.8 H$_2$O.

Calc C : 75.36% H: 7.06% N: 8.51%

Found C: 75.37% H: 6.78% N; 8.24%

(±) 46b: ¹H NMR consistent with chemical structure. HPLC Analysis Vydac; C18; diameter=4.6 mm; length=15 cm; gradient=CH$_3$CN [0.1% TFA]—H$_2$O [0.1% TFA], 5%–95%, 95%–5% over 20 min. 1.5 ml/min. flow rate; focus=215 nm, RT=10.40 min.

Analysis solvate MW 535.435 0.35 CHCl$_3$.

Calc C: 72.56% H: 6.65% N: 7.85%
Found C: 72.65% H: 6.76% N; 8.03%

EXAMPLE 45

As a specific embodiment of an oral composition, 100 mg of the compound of Example 12 is formulated with sufficient finely divided lactose to provide a total amount of 580 to 590 mg to fill a size O hard gel capsule.

EXAMPLE 46

Screening Assay: Alpha 1a Adrenergic Receptor Binding

Membranes prepared from the stably transfected human $\alpha 1a$ cell line (ATCC CRL 11140) were used to identify compounds that bind to the human alpha 1a adrenergic receptor. These competition binding reactions (total volume=200 µl) contained 50 mM Tris-HCl pH. 7.4,5 mM EDTA, 150 mM NaCl, 100 pM [$^{125}$I]-HEAT, membranes prepared from the $\alpha 1a$ cell line and increasing amounts of unlabeled ligand. Reactions were incubated at room temperature for one hour with shaking. Reactions were filtered onto Whatman GF/C glass fiber filters with a Inotec 96 well cell harvester. Filters were washed three times with ice cold buffer and bound radioactivity was determined (Ki). Representative compounds of the present invention were found to have Ki values $\leq 50$ nM.

EXAMPLE 47

Selective Binding Assays

Membranes prepared from stably transfected human $a_{1d}$ and $\alpha_{1b}$ cell lines (ATCC CRL 11138 and CRL 11139, respectively) were used to identify compounds that selectively bind to the human alpha 1a adrenergic receptor. These competition binding reactions (total volume=200 µl) contained 50 mM Tris-HCl pH. 7.4, 5 mM EDTA, 150 mM NaCl, 100 pM [$^{125}$I]-HEAT, membranes prepared from cell lines transfected with the respective alpha 1 subtype expression plasmid and increasing amounts of unlabeled ligand. Reactions were incubated at room temperature for one hour with shaking. Reactions were filtered onto Whatman GF/C glass fiber filters with a Inotec 96 well cell harvester. Filters were washed three times with ice cold buffer and bound radioactivity was determined (Ki).

EXAMPLE 48

Exemplary Counterscreens
1. Assay Title: Dopamine D2, D3, D4 in vitro screen
Objective of the Assay
The objective of this assay is to eliminate agents which specifically affect binding of [3H] spiperone to cells expressing human dopamine receptors D2, D3 or D4.
Method
Modified from VanTol et al (1991); Nature (Vol 350) Pg 610–613.

Frozen pellets containing specific dopamine receptor subtypes stably expressed in clonal cell lines are lysed in 2 ml lysing buffer (10 mM Tris-HCl/5 mM Mg, pH 7.4). Pellets obtained after centrifuging these membranes (15'at 24,450 rpm) are resuspended in 50 mM Tris-HCl pH 7.4 containing EDTA, MgCl[2], KCl, NaCl, CaCl[2]and ascorbate to give a 1 Mg/mL suspension. The assay is initiated by adding 50–75 µg membranes in a total volume of 500 µl containing 0.2 nM [3H]-spiperone. Non-specific binding is defined using 10 µM apomorphine. The assay is terminated after a 2 hour incubation at room temperature by rapid filtration over GF/B filters presoaked in 0.3% PEI, using 50 mM Tris-HCl pH 7.4.
2. Assay Title: Serotonin 5HT1a
Objective of the Assay
The objective of this assay is to eliminate agents which specifically affect binding to cloned human 5HT1a receptor
Method
Modified from Schelegel and Peroutka *Biochemical Pharmacology* 35: 1943–1949 (1 986).

Mammalian cells expressing cloned human 5HT1a receptors are lysed in ice-cold 5 mM Tris-HCl, 2 mM EDTA (pH 7.4) and homogenized with a polytron homogenizer. The homogenate is centrifuged at 1000×g for 30', and then the supernatant is centrifuged again at 38,000×g for 30'. The binding assay contains 0.25 nM [3H]8-OH-DPAT (8-hydroxy-2-dipropylamino-1,2,3,4-tetrahydronaphthalene) in 50 mM Tris-HCl, 4 mM $CaCl_2$ and 1 mg/ml ascorbate. Non-specific binding is defined using 10 µMM propranolol. The assay is terminated after a 1 hour incubation at room temperature by rapid filtration over GF/Cfilters

EXAMPLE 49

Exemplary Functional Assays

In order to confirm the specificity of compounds for the human alpha 1a adrenergic receptor and to define the biological activity of the compounds, the following functional tests may be performed:
1. In vitro Rat, Dog and Human Prostate and Dog Urethra Taconic Farms Sprague-Dawley male rats, weighing 250–400 grams are sacrificed by cervical dislocation under anesthesia (methohexital; 50 mg/kg, i.p.). An incision is made into the lower abdomen to remove the ventral lobes of the prostate. Each prostate removed from a mongrel dog is cut into 6–8 pieces longitudinally along the urethra opening and stored in ice-cold oxygenated Krebs solution overnight before use if necessary. Dog urethra proximal to prostate is cut into approximately 5 mm rings, the rings are then cut open for contractile measurement of circular muscles. Human prostate chips from transurethral surgery of benign prostate hyperplasia are also stored overnight in ice-cold Krebs solution if needed.

The tissue is placed in a Petri dish containing oxygenated Krebs solution [NaCl, 118 mM; KCl, 4.7 mM; $CaCl_2$, 2.5 mM; $KH_2PO_4$, 1.2 mM; $MgSO_4$, 1.2 mM; $NaHCO_3$, 2.0 mM; dextrose, 11 mM] warmed to 37° C. Excess lipid material and connective tissue are carefully removed. Tissue segments are attached to glass tissue holders with 4-0 surgical silk and placed in a 5 ml jacketed tissue bath containing Krebs buffer at 37° C., bubbled with 5% $CO_2$/95% $O_2$. The tissues are connected to a Statham-Gould force transducer; 1 gram (rat, human) or 1.5 gram (dog) of tension is applied and the tissues are allowed to equilibrate for one hour. Contractions are recorded on a Hewlett-Packard 7700 series strip chart recorder.

After a single priming dose of 3 µM (for rat), 10 µM (for dog) and 20 µM (for human) of phenylephrine, a cumulative concentration response curve to an agonist is generated; the tissues are washed every 10 minutes for one hour. Vehicle or antagonist is added to the bath and allowed to incubate for one hour, then another cumulative concentration response curve to the agonist is generated.

$EC_{50}$ values are calculated for each group using GraphPad Inplot software. $pA_2$ (-log Kb) values were obtained from Schild plot when three or more concentrations were tested. When less than three concentrations of antagonist are tested, $K_b$ values are calculated according to the following formula $$K_b = [B]/x-1$$

where x is the ratio of $EC_{50}$ of agonist in the presence and absence of antagonist and [B] is the antagonist concentration.

2. Measurement of Intra-Urethral Pressure in Anesthetized Dogs

PURPOSE: Benign prostatic hyperplasia causes a decreased urine flow rate that may be produced by both passive physical obstruction of the prostatic urethra from increased prostate mass as well as active obstruction due to prostatic contraction. Alpha adrenergic receptor antagonists such as prazosin and terazosin prevent active prostatic contraction, thus improve urine flow rate and provide symptomatic relief in man. However, these are non-selective alpha-1 receptor antagonists which also have pronounced vascular effects. Because we have identified the alpha-1a receptor subtype as the predominent subtype in the human prostate, it is now possible to specifically target this receptor to inhibit prostatic contraction without concomitant changes in the vasculature. The following model is used to measure adrenergically mediated changes in intra-urethral pressure and arterial pressure in anesthetized dogs in order to evaluate the efficacy and potency of selective alpha adrenergic receptor antagonists. The goals are to: 1) identify the alpha-1 receptor subtypes responsible for prostatic/urethral contraction and vascular responses, and 2) use this model to evaluate novel selective alpha adrenergic antagonists. Novel and standard alpha adrenergic antagonists may be evaluated in this manner.

Methods

Male mongrel dogs (7–12 kg) are used in this study. The dogs are anesthetized with pentobarbital sodium (35 mg/kg, i.v. plus 4 mg/kg/hr iv infusion). An endotracheal tube is inserted and the animal ventilated with room air using a Harvard instruments positive displacement large animal ventilator. Catheters (PE 240 or 260) are placed in the aorta via the femoral artery and vena cava via the femoral veins (2 catheters, one in each vein) for the measurement of arterial pressure and the administration of drugs, respectively. A supra-pubic incision ~½ inch lateral to the penis is made to expose the urethers, bladder and urethra. The urethers are ligated and cannulated so that urine flows freely into beakers. The dome of the bladder is retracted to facilitate dissection of the proximal and distal urethra. Umbilical tape is passed beneath the urethra at the bladder neck and another piece of umbilical tape is placed under the distal urethra approximately 1–2 cm distal to the prostate. The bladder is incised and a Millar micro-tip pressure transducer is advanced into the urethra. The bladder incision is sutured with 2-0 or 3-0 silk (purse-string suture) to hold the transducer. The tip of the transducer is placed in the prostatic urethra and the position of the Millar catheter is verified by gently squeezing the prostate and noting the large change in urethral pressure.

Phenylephrine, an alpha-1 adrenergic agonist, is administered (0.1–100 ug/kg, iv; 0.05 ml/kg volume) in order to construct dose response curves for changes in intra-urethral and arterial pressure. Following administration of increasing doses of an alpha adrenergic antagonist (or vehicle), the effects of phenylephrine on arterial pressure and intra-urethral pressure are re-evaluated. Four or five phenylephrine dose-response curves are generated in each animal (one control, three or four doses of antagonist or vehicle). The relative antagonist potency on phenylephrine induced changes in arterial and intra-urethral pressure are determined by Schild analysis. The family of averaged curves are fit simultaneously (using ALLFIT software package) with a four paramenter logistic equation constraining the slope, minimum response, and maximum response to be constant among curves. The dose ratios for the antagonist doses (rightward shift in the dose-response curves from control) are calculated as the ratio of the $ED_{50}$'s for the respective curves. These dose-ratios are then used to construct a Schild plot and the Kb (expressed as ug/kg, iv) determined. The Kb (dose of antagonist causing a 2-fold rightward shift of the phenylephrine dose-response curve) is used to compare the relative potency of the antagonists on inhibiting phenylephrine responses for intra-urethral and arterial pressure. The relative selectivity is calculated as the ratio of arterial pressure and intra-urethral pressure Kb's. Effects of the alpha-i antagonists on baseline arterial pressure are also monitored. Comparison of the relative antagonist potency on changes in arterial pressure and intra-urethral pressure provide insight as to whether the alpha receptor subtype responsible for increasing intra-urethral pressure is also present in the systemic vasculature. According to this method, one is able to confirm the selectivity of alpha 1a adrenergic receptor antagonists that prevent the increase in intra-urethral pressure to phenylephrine without any activity at the vasculature.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of the formula:

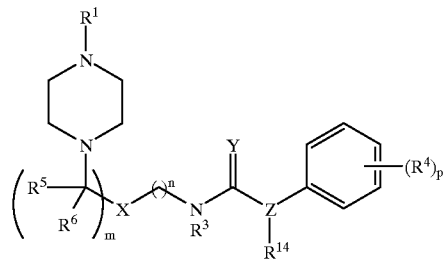

wherein

X is selected from $CHOR^5$, CHF, $CR^5R^6$, $CF_2$, $CHCHF^2$, or $C=CF^2$;

Y is selected from oxygen, $NR^8$ or sulfur;

Z is selected from CH, $CCO_2R^5$, $C(CH_2)_{1-3}CO_2R^5$, $COR^{12}$, $CNR^{12}R^{13}$ or $C(CH_2)qCH_2N(R^5)_2$;

$R^1$ is selected from unsubstituted, mono- or poly-substituted phenyl where the substituents on the phenyl are independently selected from halogen, cyano, $OR^5$, or $C_{1-4}$ alkyl; provided that when $R^1$ is mono-substituted phenyl and the substituent is $OR^5$, the substituent is other than in the 2-position on the phenyl ring;

$R^3$ is selected from hydrogen, cyano, $CO_2R^5$, $CON(R^5)_2$, $C_{1-8}$ alkyl, $C_{3-8}$ cycloalkyl or $(CH_2)_{1-3}CO_2R^5$;

$R^4$ is selected from hydrogen, $OR^5$, $C_{1-8}$ alkyl, or halogen $R^5$ and $R^6$ are each independently selected from hydrogen, $C_{1-8}$ alkyl, $C_{3-8}$ cycloalkyl, halogen substituted $C_{1-4}$ alkyl and halogen substituted $C_{3-8}$ cycloalkyl;

$R^8$ is selected from hydrogen, cyano or $SO_2R^5$;

$R^{12}$ and $R^{13}$ are each independently selected from hydrogen, $C_{1-8}$ alkyl, $C_{3-8}$ cycloalkyl, CHO, $COR^5$, $CONR^5R^6$, and $(CH_2)qOR^5$;

$R^{14}$ is selected from hydrogen, $C_{1-8}$ alkyl, $C_{3-8}$ cycloalkyl, $C_{1-4}$ alkoxy, morpholinyl, piperazinyl, d-valerolactamyl, 2-pyrrolidonyl, thiophenyl, furanyl, pyridinyl, naphthyl or unsubstituted, mono- or poly-substituted phenyl where the substituents on the phenyl are independently selected from $C_{1-4}$ alkyl, $OR^5$ or halogen; m, n and q are each independently an integer of from zero to three, provided that when m and n are both zero, then X is selected from CHF, $CR^5R^6$, $CF_2$, $CHCHF_2$, or C=$CF_2$; and p is an integer of from zero to five;

and further provided that when Z is CH and $R^{14}$ is hydrogen, then $R^1$ is not unsubstituted phenyl;

or a pharmaceutically acceptable salt thereof.

2. The compound of claim 1, wherein $R^1$ is selected from unsubstituted, mono- or poly-substituted phenyl where the substituents on the phenyl are independently selected from halogen, cyano, or $C_{1-4}$ alkyl;

and p is an integer from 0 to 3;

and further provided that when Z is CH and $R^{14}$ is hydrogen, then $R^1$ is not unsubstituted phenyl;

or a pharmaceutically acceptable salt thereof.

3. The compound of claim 1 wherein $R^{12}$ and $R^{13}$ are each independently selected from hydrogen and $C_{1-8}$ alkyl;

and further provided that when Z is CH and $R^{14}$ is hydrogen, then $R^1$ is not unsubstituted phenyl;

or a pharmaceutically acceptable salt thereof.

4. The compound according to claim 1, wherein

X is selected from $CHOR^5$, CHF, $CR^5R^6$, $CF_2$, $CHCHF_2$, or C=$CF_2$;

Y is selected from oxygen, $NR^8$ or sulfur;

Z is selected from CH, $CCO_2R^5$, $C(CH_2)_{1-3}CO_2R^5$, $COR^{12}$, $CNR^{12}R^{13}$ or $C(CH_2)qCH_2N(R^5)_2$;

$R^1$ is mono- or poly-substituted phenyl where the substituents on the phenyl are independently selected from halogen, cyano, $OR^5$, or $C_{1-4}$ alkyl; provided that when $R^1$ is mono-substituted phenyl and the substituent is $OR^5$, the substituent is other than in the 2-position on the phenyl ring;

$R^3$ is selected from hydrogen, cyano, $CO_2R^5$, $CON(R^5)_2$, $C_{1-8}$ alkyl, $C_{3-8}$ cycloalkyl or $(CH_2)_{1-3}CO_2R^5$;

$R^4$ is selected from hydrogen, $OR^5$, $C_{1-8}$ alkyl, or halogen $R^5$ and $R^6$ are each independently selected from hydrogen, $C_{1-8}$ alkyl, $C_{3-8}$ cycloalkyl, halogen substituted $C_{1-4}$ alkyl and halogen substituted $C_{3-8}$ cycloalkyl;

$R^8$ is selected from hydrogen, cyano or $SO_2R^5$;

$R^{12}$ and $R^{13}$ are each independently selected from hydrogen, $C_{1-8}$ alkyl, $C_{3-8}$ cycloalkyl, CHO, $COR^5$, $CONR^5R^6$, and $(CH_2)qOR^5$;

$R^{14}$ is selected from hydrogen, $C_{1-8}$ alkyl, $C_{3-8}$ cycloalkyl, $C_{1-4}$ alkoxy, morpholinyl, piperazinyl, d-valerolactamyl, 2-pyrrolidonyl, thiophenyl, furanyl, pyridinyl, naphthyl or unsubstituted, mono- or poly-substituted phenyl where the substituents on the phenyl are independently selected from $C_{1-4}$ alkyl, $OR^5$ or halogen;

m, n and q are each independently an integer of from zero to three, provided that when m and n are both zero, then X is selected from CHF, $CR^5R^6$, $CF_2$, $CHCHF_2$, or C=$CF_2$; and p is an integer of from zero to five;

or a pharmaceutically acceptable salt thereof.

5. The compound according to claim 4, wherein $R^1$ is mono- or poly-substituted phenyl where the substituents on the phenyl are independently selected from halogen, cyano, or $C_{1-4}$ alkyl;

and p is an integer from 0 to 3;

or a pharmaceutically acceptable salt thereof.

6. The compound of claim 4 wherein $R^{12}$ and $R^{13}$ are each independently selected from hydrogen and $C_{1-8}$ alkyl;

or a pharmaceutically acceptable salt thereof.

7. The compound according to claim 1, wherein the compound is or a pharmaceutically acceptable salt thereof.

8. The compound according to claim 3, wherein $R^5$ is hydrogen; and $R^6$ is hydrogen;

and further provided that when Z is CH and $R^{14}$ is hydrogen, then $R^1$ is not unsubstituted phenyl;

or a pharmaceutically acceptable salt thereof.

9. A pharmaceutical composition made by combining a therapeutically effective amount of a compound of claim 1 and a pharmaceutically acceptable carrier.

10. A pharmaceutical composition comprising an alpha 1a adrenergic receptor antagonistic effective amount of the compound of claim 1 and a pharmaceutically acceptable carrier.

11. The composition of claim 10 further comprising a therapeutically effective amount of a testosterone 5-alpha reductase inhibitor.

12. The composition of claim 11, wherein the testosterone 5-alpha reductase inhibitor is a type 1, a type 2, both a type 1 and a type 2 or a dual type 1 and type 2 testosterone 5-alpha reductase inhibitor.

13. The composition of claim 12, wherein the testosterone 5-alpha reductase inhibitor is a type 2 testosterone 5-alpha reductase inhibitor.

14. The composition of claim 13, wherein the testosterone 5-alpha reductase inhibitor is finasteride.

15. A method of treating benign prostatic hyperplasia in a subject in need thereof which comprises administering to the subject an alpha 1a adrenergic receptor antagonistic effective amount of the compound of claim 1.

16. The method of claim 15, wherein the effective amount of the compound additionally does not cause a fall in blood pressure.

17. The method of claim 15, wherein the compound is administered in combination with a testosterone 5-alpha reductase inhibitor.

18. The method of claim 17, wherein the testosterone 5-alpha reductase inhibitor is finasteride.

19. A method of treating benign prostatic hyperplasia in a subject in need thereof which comprises administering a therapeutically effective amount of the composition of claim 10.

20. The method of claim 19, wherein the composition further comprises a therapeutically effective amount of a testosterone 5-alpha reductase inhibitor.

21. A method of relaxing urethral smooth muscle in a subject in need thereof which comprises administering to the subject a therapeutically effective amount of the compound of claim 1.

22. The method of claim 21, wherein the compound additionally does not cause a fall in blood pressure at dosages effective to relax urethral smooth muscle.

23. The method of claim 21, wherein the compound is administered in combination with a testosterone 5-alpha reductase inhibitor.

24. The method of claim 23, wherein the testosterone 5-alpha reductase inhibitor is finasteride.

25. A method of treating a urinary obstruction caused by benign prostatic hyperplasia in a subject which comprises administering to said subject an alpha 1a adrenergic receptor antagonistic effective amount of the compound of claim 1.

* * * * *